(12) United States Patent
Farrand

(10) Patent No.: US 6,495,217 B2
(45) Date of Patent: *Dec. 17, 2002

(54) CHIRAL COMPOUNDS

(75) Inventor: Louise Farrand, Manchester (GB)

(73) Assignee: Merck Patent GmbH, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/411,380

(22) Filed: Oct. 4, 1999

(65) Prior Publication Data

US 2002/0005505 A1 Jan. 17, 2002

(30) Foreign Application Priority Data

Oct. 2, 1998 (EP) ............................................. 98118646

(51) Int. Cl.$^7$ ......................... C09K 19/34; C09K 19/30; C09K 19/12; C09K 19/20; C09K 19/38; C07C 69/76; C07D 317/00

(52) U.S. Cl. ........................... 428/1.1; 428/1.2; 428/1.3; 428/1.5; 252/299.61; 252/299.65; 252/299.64; 252/299.66; 252/299.67; 549/450; 560/60; 560/126

(58) Field of Search ....................... 252/299.61, 299.63, 252/299.64, 299.65, 299.66, 299.67; 428/1.1, 1.2, 1.3, 1.5; 549/450; 560/60, 126

(56) References Cited

U.S. PATENT DOCUMENTS 5,869,697 A * 2/1999 Bhushan et al. ............... 549/34

FOREIGN PATENT DOCUMENTS

| EP | 0 351 746 | | 1/1990 |
|---|---|---|---|
| EP | 441213 | * | 1/1991 |
| WO | 89/02428 | * | 3/1989 |
| WO | 89/05298 | * | 6/1999 |

OTHER PUBLICATIONS

Caplus 1995: 833617.*
English Abstract of EP 0 351 746, 1990.
Duebal et al., *"Three Classes of New Chiral Dopants: Synthesis and Physical Qualification as Dopants for Practical FLC–Mixtures,"* Jap. J. Appl. Phys. 27, vol. 12(2), 1988, 2241–2244.

* cited by examiner

*Primary Examiner*—Shean C. Wu
(74) *Attorney, Agent, or Firm*—Millen, White, Zelano & Branigan, P.C.

(57) ABSTRACT

The invention relates to chiral compounds of formula I

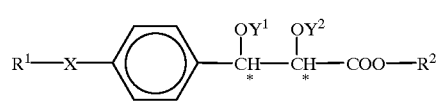

wherein $R^1$, $R^2$, X, $Y^1$ and $Y^2$ have the meanings defined herein, as well as to liquid crystalline mixtures comprising at least one chiral compound of formula I. The invention also relates to chiral linear or crosslinked liquid crystalline polymers obtainable by polymerizing a polymerizable mixture comprising at least one chiral compound of formula I, and to the use of chiral compounds of formula I and mixtures and polymers obtained thereof in liquid crystal displays, such as STN, TN, AMD-TN, temperature compensation, guest-host, phase change or surface stabilized or polymer stabilized cholesteric texture (SSCT, PSCT) displays, in active and passive optical elements like polarizers, compensators, alignment layers, color filters or holographic elements in adhesives, synthetic resins with anisotropic mechanical properties, cosmetics, diagnostics, liquid crystal pigments, for decorative and security applications, in non-linear optics, optical information storage or as chiral dopants, and to a liquid crystal display comprising a mixture comprising at least one chiral compound of formula I.

65 Claims, No Drawings

CHIRAL COMPOUNDS

The invention relates to chiral compounds of formula I

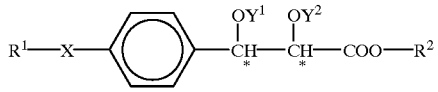

wherein $Y^1$ is —Y—$R^3$ and $Y^2$ is —Y—$R^4$, or alternatively $Y^1$ and $Y^2$ form together the bivalent radical —CO— or —C($XR^3$)($XR^4$)—;

$R^1$, $R^2$, $R^3$ and $R^4$ are independently of each other H, CN, halogen, or an aromatic, aliphatic or araliphatic group with 1 to 50 C atoms;

X is in each case independently —O—, —S—, —CO—, —COO—, —OCO—, —OCO—O—, —CO—NH—, —NH—CO—, —OCH$_2$—, —CH$_2$O—, —CH=CH—, —C≡C, —SCH$_2$—, —CH$_2$S—, —CH=CH—COO—, —OOC—CH=CH— or a single bond; and Y is in each case independently —CO—, —COO—, —CO—NH—, —CO—CH=CH— or a single bond.

The invention also relates to a liquid crystalline mixture containing at least one chiral compound of formula I.

The invention also relates to a polymerizable liquid crystalline mixture comprising at least one chiral compound of formula I and at least one polymerizable mesogenic compound.

The invention furthermore relates to the use of chiral compounds of formula I and liquid crystalline mixtures and polymers obtained thereof in liquid crystal displays, such as STN, TN, AMD-TN, temperature compensation, guest-host, phase change or surface stabilized or polymer stabilized cholesteric texture (SSCT, PSCT) displays, in active and passive optical elements like polarizers, compensators, alignment layers, color filters or holographic elements, in adhesive, synthetic resins with anisotropic mechanical properties, cosmetics, diagnostics, liquid crystal pigments, for decorative and security applications, in nonlinear optics, optical information storage or as chiral dopants, The invention also relates to a liquid crystal display comprising a mixture comprising at least one chiral compound of formula I.

Chiral compounds can be used as dopants to induce or enhance a helical twist of the molecules of a liquid crystalline mixture that can be used for example in liquid crystal displays. The pitch p of the molecular helix in the first approximation, which is sufficient for most practical applications, is inversely proportional to the concentration c of the chiral dopant in the liquid crystal host mixture according to equation (1):

$$p = \frac{1}{HTP} \cdot \frac{1}{C} \qquad (1)$$

The proportionality factor is the helical twisting power (HTP) of the chiral dopant.

For many applications it is desirable to have LC mixtures that exhibit a twist. Among these are, e.g., phase-change displays, guest-host displays, passive and active matrix TN and STN displays like AMD-TN, including such displays with temperature compensated characteristics, e.g., by appropriate selection of the cholesteric compounds according to the invention either alone or in combination with further chiral dopants. For these applications it is advantageous to have available a chiral dopant with a high HTP in order to reduce the amount of dopant needed to induce the desired pitch.

For some applications it is desired to have LC mixtures that exhibit a strong helical twist and thereby a short pitch length. For example, in liquid crystalline mixtures that are used in selectively reflecting cholesteric displays, the pitch has to be selected such that the maximum of the wavelength reflected by the cholesteric helix is in the range of visible light. Another possible application are polymer films with a chiral liquid crystalline phase for optical elements, such as cholesteric broadband polarizers or chiral liquid crystalline retardation films.

As can be seen from equation (1), a short pitch can be achieved by using high amounts of dopant or by using a dopant with a high HTP.

However, the chiral dopants of prior art often exhibit low values of the HTP, so that high amounts of dopant are needed. This is a disadvantage because chiral dopants can be used only as pure enantiomers and are therefore expensive and difficult to synthesize.

Furthermore, when using chiral dopants of prior art in high amounts, they often negatively affect the properties of the liquid crystalline host mixture, such as, e.g., the dielectric anisotrophy Δε, the viscosity, the driving voltage or the switching times.

Thus, there is a considerable demand for chiral compounds with a high HTP which are easy to synthesize, which can be used in low amounts, show improved temperature stability of the cholesteric pitch, e.g., for utilizing a constant reflection wavelength and do not affect the properties of the liquid crystalline host mixture.

The invention has the aim of providing chiral compounds having these properties, but which do not have the disadvantages of the chiral dopants of the state of the art as discussed above.

Another aim of the invention is to extend the poor of chiral compounds that can be used as dopants available to the expert.

Upon further study of the specification and appended claims, further objects and advantages of this invention will become apparent to those skilled in the art.

It has been found that these aims can be achieved by providing chiral compounds according to formula I.

The inventive chiral compounds bear several advantages. Thus, they contain a chiral structure element exhibiting two centers of chirality and thus exhibit a high twisting power. Also, enantiomerically pure compounds of formula I are easy to prepare from cheap, readily available starting materials. The preparation methods are also suitable for large scale production. Furthermore, it is possible to prepare the R,S and S,R enantiomers which can be used to produce a cholesteric phase with either a right or a left-handed helix. The availability of both helices can be a considerable advantage, e.g., for the use in security film applications.

The EP 0 441 213-B1 describes chiral compounds comprising a 1,3-dioxolane group attached in 2-position to a mesogenic group, but does not specifically disclose compounds of formula I of the present invention.

Thus, an object of this invention are chiral compounds of formula I

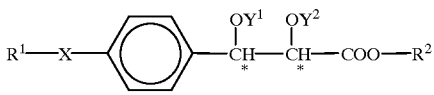

I wherein
- Y$^1$ is —Y—R$^3$ and Y$^2$ is —Y—R$^4$, or alternatively Y$^1$ and Y$^2$ form together the bivalent radical —CO— or —C(XR$^3$)(XR$^4$)—,
- R$^1$, R$^2$, R$^3$ and R$^4$ are independently of each other H, CN, halogen or an aromatic, aliphatic group with up to 50 C atoms;
- X is in each case independently —O—, —S—, —CO—, —COO—, —OCO—, —OCO—O, —CO—NH—, —NH—CO—, —OCH$_2$—, —CH$_2$O—, —CH=CH—, —C≡C—, —SCH$_2$—, —CH$_2$S—, —CH=CH—COO—, —OOC—CH=CH— or a single bond; and
- Y is in each case independently —CO—, —COO—, —CO—NH—, —CO—CH=CH— or a single bond.

Another object of the invention is a liquid crystalline mixture containing at least one chiral compound of formula I.

Another object of the invention is a polymerizable liquid crystalline mixture comprising at least one chiral compound of formula I and at least one polymerizable mesogenic compound having at least one polymerizable functional group. Another object of the invention is a chiral linear or crosslinked crystalline polymer obtainable by polymerizing such a polymerizable mixture.

A further object of the invention is the use of a chiral compound, mixture or polymer as described above in liquid crystal displays, such as STN, TN, AMD-TN, temperature compensation, guest-host, phase change or surface stabilized or polymer stabilized cholesteric texture (SSCT, PSCT) displays, in active and passive optical elements like polarizers, compensators, alignment layers, color filters or in holographic elements, in adhesives, synthetic resins with anisotropic mechanical properties, cosmetics, diagnostics, liquid crystal pigments, for decorative and security applications, in nonlinear optics, optical information storage or as chiral dopants.

Yet another object of the invention is a liquid crystal display comprising a liquid crystalline mixture or a polymerizable liquid crystalline mixture comprising at least one chiral compound of formula I.

The inventive chiral compounds can additionally be mesogenic or even liquid crystalline, i.e., they can induce or enhance mesophase behavior for example in admixture with other compounds, or even exhibit one or more mesophases themselves. It is also possible that the inventive compounds show mesophase behavior only in mixtures with other compounds, or, in case of polymerizable compounds, when being (co)polymerized. Mesogenic inventive chiral compounds are especially preferred.

The groups R$^1$, R$^2$, R$^3$ and R$^4$ can be aromatic or aliphatic groups or araliphatic groups, i.e., combinations thereof.

The aliphatic groups containing straight-chain, branched-chain, and/or cyclic structures. Suitable aliphatic groups are for example straight chain or branched alkyl groups with 1 to 50, in particular 1 to 25 C atoms, which can optionally be mono-, di- or higher substituted by F, Cl or CN, and wherein one or more nonadjacent CH$_2$ atoms can be replaced by —O—, —S—, —NH—, —CO—, —CH=CH— or —C≡C— groups. Further suitable groups are cycloaliphatic hydrocarbon groups comprising one, two or three mono- or bicyclic systems, in particular five- or six-membered rings, that may also comprise up to three hetero atoms, such as N, S and O.

The aromatic groups preferably have one, two or three mono- or bicyclic structures where each ring preferably has 5 to 6 ring members. Suitable aromatic groups are, for example, phenyl, biphenyl, terphenyl or naphthyl groups, wherein the aromatic rings may also comprise up to three hetero atoms such as N, S and O, in particular N atoms, and which can be unsubstituted or mono-, di-, tri- or higher substituted with F, Cl, CN, OH, COOH or alkyl, alkoxy, alkylcarbonyl or alkoxycarbonyl groups with up to 7 C atoms.

Particularly preferably the groups R$^1$ to R$^4$ are araliphatic groups, i.e., combinations of the aromatic and aliphatic groups as described above.

Further preferred are compounds according to formula I wherein at least one of R$^1$, R$^2$, R$^3$ and R$^4$ is an aliphatic, aromatic or araliphatic group having up to 50 C atoms in which the group is provided with a terminal polymerizable group, in particular acrylate, methacrylate, vinyl, vinyloxy or epoxy groups.

Further preferred are compounds of formula I wherein the groups R$^1$, R$^2$, R$^3$ and/or R$^4$ comprise one or more chiral C atoms in addition to the chiral structure shown in formula I. Such compounds exhibit particularly high values of the HTP.

Especially preferred are chiral compounds of formula I, wherein at least one of R$^1$, R$^2$, R$^3$ and R$^4$ is selected of formula I*

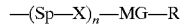   I* wherein
- Sp is in each case independently a spacer group with 1 to 20 C atoms,
- X has in each case independently one of the meanings of formula I,
- n is 0 or 1,
- MG is a mesogenic group, and
- R is in each case independently H, CN, halogen or a straight-chain or branched alkyl radical with up to 25 C atoms which may be unsubstituted, mono- or polysubstituted by halogen or CN, it being also possible for one or more nonadjacent CH$_2$ groups to be replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, or denoting P-(Sp-X)$_x$-, with Sp, X and n having one of the meanings given above and P being a polymerizable group.

Further preferred are chiral compounds wherein MG is selected of formula II

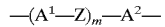   II wherein
- Z is —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO, —OCO—CH=CH—, —C≡C— or a single bond,
- A$^1$ and A$^2$ are in each case independently selected from
  a) 1,4-phenylene in which, in addition, one or more CH groups may be replaced, in each case independently, by N, b) 1,4-cyclohexylene in which, in addition, one or two nonadjacent $CH_2$ groups may be replaced, in each case independently, by O or S,
c) 1,3-dioxolane-4,5-diyl,
d) 1,4-cyclohexenylene, 1,4-bicyclo-(2,2,2)-octylene, piperidine-1,4-diyl, naphthalene-2,6-diyl, decahydronaphthalene-2,6-diyl, or
1,2,3,4-tetrahydronaphthalene-2,6-diyl, it being possible for all these groups to be unsubstituted, mono- or polysubstituted with halogen, cyano, or nitro groups or alkyl, alkoxy, alkylcarbonyl or alkoxycarbonyl groups with 1 to 7 C atoms, wherein one or more H atoms can be replaced by F or Cl, and m is 0, 1, 2 or 3.

Further preferred are chiral compounds of formula I, wherein at least one of $R^1$ $R^2$, $R^3$ and $R^4$ is denoting R as defined in formula I*.

Further preferred are chiral compounds of formula I wherein

R is alkyl or alkoxy with 1 to 12 C atoms, at least one of the groups R is denoting P-(Sp-X)$_n$-, with P, Sp, X and n having each independently one of the meanings given in formula I*, Further preferred are compounds of formula I wherein at least one of, especially both $R^1$ and $R^2$ are -(Sp-X)$_n$-MG-R, with P, Sp, X and n having the meaning given in formula I.

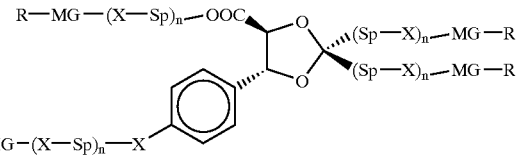
Ia

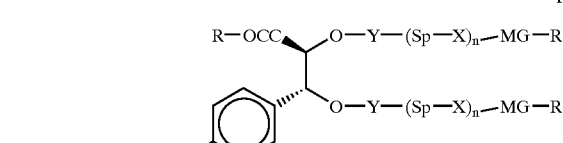
Ib

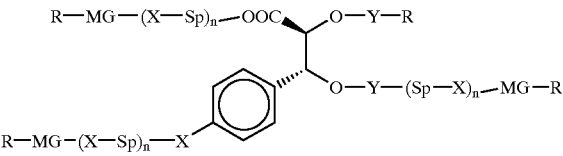
Ic

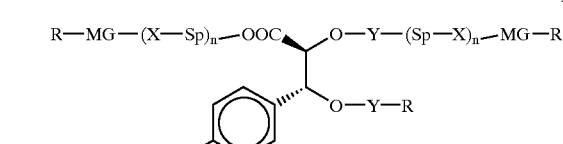
Id

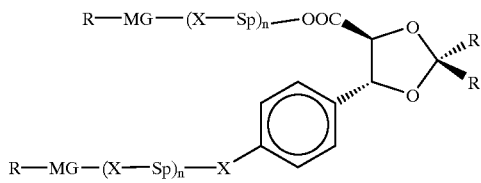
Ie

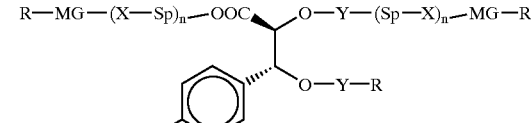
If

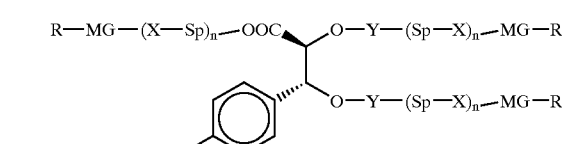
Ig

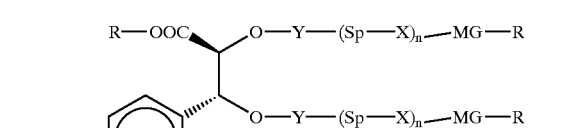
Ih

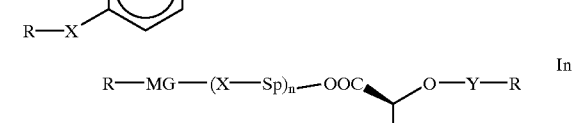
Ii

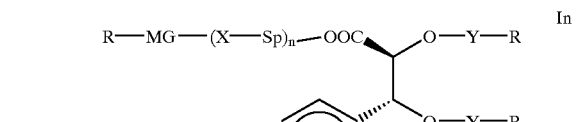
Ik

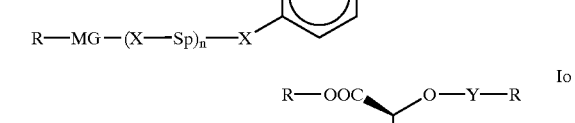
Im

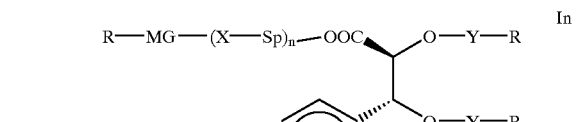
In

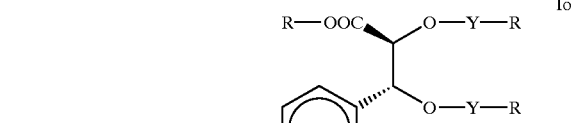
Io

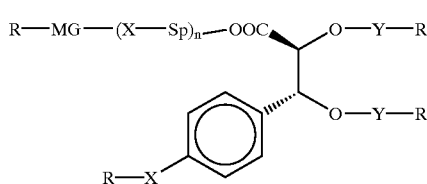

wherein X and Y have each independently one of the meanings of formula I and Sp, MG, n and R have each independently one of the meanings of formula I*.

Of these preferred compounds particularly preferred are those of formula Ia, Ib, Ic, Id, Im, In and Ip.

Of the inventive compounds especially preferred are those wherein MG incorporates one, two or three five- or six-membered rings.

Further preferred compounds are those in which R is F, Cl, cyano, alkyl or alkoxy with 1 to 12 C atoms and MG is of formula II wherein Z is —COO—, —OCO—, —CH$_2$—CH$_2$— or a single bond.

X is preferably —O—, —CO—, —COO—, —OCO—, —CH$_2$O—, —OCH$_2$— or a single bond, in particular —O—, —COO—, —OCO— or a single bond.

Y is preferably —CO— or a single bond.

Particularly preferred compounds are those wherein MG is of formula II, and A$^1$ and A$^2$ are selected of 1,4-phenylene and trans-1,4-cyclohexylene, these rings being unsubstituted or substituted in 1 to 4 positions with F, Cl, CN or alkyl, alkoxy or alkoxycarbonyl with 1 to 4 C-atoms. From these preferred compounds, especially preferred are those wherein MG is a biphenyl or cyclohexylphenyl group.

Further preferred compounds are those wherein MG is comprising one or two 1,3-dioxolane-4,5-diyl rings, in particular wherein the 1,3-dioxolane-4,5-diyl groups are linked to an ester group.

A smaller group of preferred mesogenic groups MG of formula II is listed below. For reasons of simplicity, Phe in these groups is 1,4-phenylene, Phe L is a 1,4-phenylene group which is substituted by at least one group L, with L being F, Cl, CN, NO$_2$ or an optionally fluorinated alkyl, alkoxy or alkanoyl group with 1 to 4 C atoms, and Cyc is 1,4-cyclohexylene. The list of preferred mesogenic groups is comprising the formulae II-1 to II-27 as well as their mirror images

| | |
|---|---|
| -Phe- | II-1 |
| -Cyc- | II-2 |
| -PheL- | II-3 |
| -Phe-Z-Phe- | II-4 |
| -Phe-Z-Cyc- | II-5 |
| -Cyc-Z-Cyc- | II-6 |
| -PheL-Z-Phe- | II-7 |
| -PheL-Z-Cyc- | II-8 |
| -PheL-Z-PheL- | II-9 |
| -Phe-Z-Phe-Z-Phe- | II-10 |
| -Phe-Z-Phe-Z-Cyc- | II-11 |
| -Phe-Z-Cyc-Z-Phe- | II-12 |
| -Cyc-Z-Phe-Z-Cyc- | II-13 |
| -Phe-Z-Cyc-Z-Cyc- | II-14 |
| -Cyc-Z-Cyc-Z-Cyc- | II-15 |
| -Phe-Z-Phe-Z-PheL- | II-16 |
| -Phe-Z-PheL-Z-Phe- | II-17 |
| -PheL-Z-Phe-Z-PheL- | II-18 |
| -PheL-Z-PheL-Z-Phe- | II-19 |
| -PheL-Z-PheL-Z-PheL- | II-20 |
| -Phe-Z-PheL-Z-Cyc- | II-21 |
| -Phe-Z-Cyc-Z-PheL- | II-22 |
| -Cyc-Z-Phe-Z-PheL- | II-23 |
| -PheL-Z-Cyc-Z-PheL- | II-24 |
| -PheL-Z-PheL-Z-Cyc- | II-25 |
| -PheL-Z-Cyc-Z-Cyc- | II-26 |
| -Cyc-Z-PheL-Z-Cyc- | II-27 |

Bicyclic and tricyclic mesogenic groups MG are preferred.

Further preferred are compounds wherein MG is selected of formula II-7, II-8, II-9 or II-16 to II-27, and L is F, Cl, CH$_3$, OCH$_3$, OCF$_3$ or CN.

In the above list of preferred groups Z has the meaning given in formula II described above. Preferably Z is —COO—, —OCO—, —CH$_2$CH$_2$—, —CH=CH—COO— or a single bond.

L is preferably F, Cl, CN, NO$_2$, CH$_3$, C$_2$H$_5$, OCH$_3$, OC$_2$H$_5$, COCH$_3$, COC$_2$H$_5$, CF$_3$, OCF$_3$, OCHF$_2$, OC$_2$F$_5$, in particular F, Cl, CN, CH$_3$, C$_2$H$_5$, OCH$_3$, COCH$_3$ and OCF$_3$, most preferably F, CH$_3$, OCH$_3$ and COCH$_3$.

Particularly preferred are chiral compounds wherein MG is selected from the following formulae and their mirror images

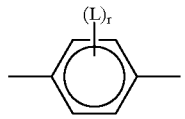

IIa

IIb

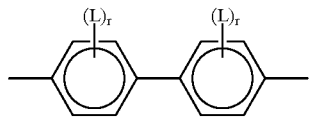

IIc

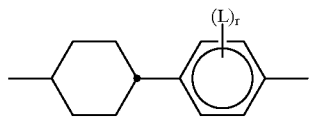

IId

IIe

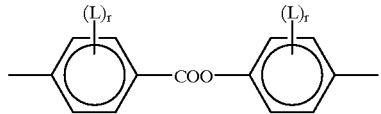

IIf

IIg

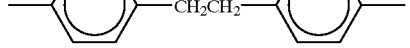

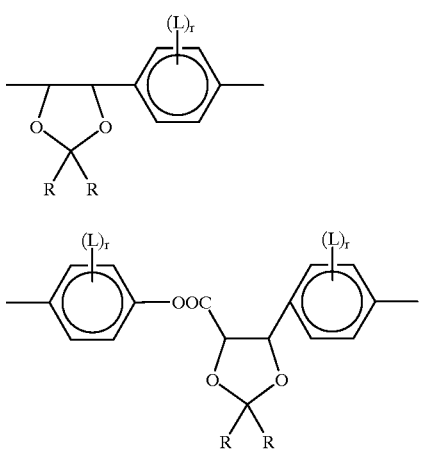

IIh

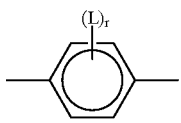

IIi

In these formulae R and L have the meaning given above and r is 0, 1 or 2.

The group

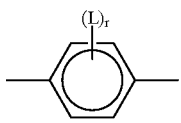

in these preferred formulae is very preferably denoting

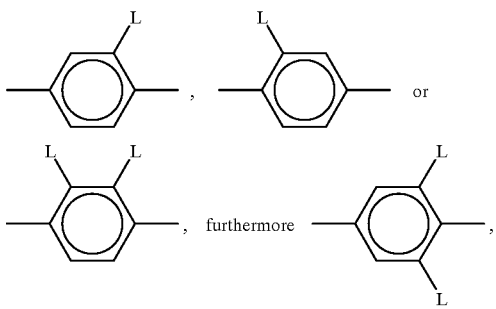

with L having each independently one of the meanings given above.

R in the preferred compounds described above is particularly preferably CN, F, Cl, OCF$_3$ or an alkyl or alkoxy group with 1 to 12 C atoms. Straight-chain alkyl or alkoxy groups are especially preferred.

If R is an alkyl or alkoxy radical, i.e. where the terminal CH$_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

R can also be an oxaalkyl group, i.e., where one CH$_2$ group is replaced by —O—. Preferred oxaalkyl groups are straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9 oxadecyl, for example.

In the chiral compounds of formula I R may be an achiral or a chiral group. In case of a chiral group it is preferably selected according to the following formula III:

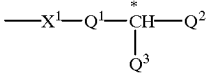

III wherein

X$^1$ is —O—, —S—, —CO—, —COO—, —OCO—, —OCOO— or a single bond,

Q$^1$ is an alkylene or alkylene-oxy group with 1 to 10 C atoms or a single bond, Q$^2$ is an alkyl or alkoxy group with 1 to 10 C atoms which may be unsubstituted, mono- or polysubstituted by halogen or CN, it being also possible for one or more non-adjacent CH$_2$ groups to be replaced, in each case independently from one another, by —C≡C—, —O—, —S—, —NH—, —N(CH$_3$)—, —CO—, —COO—, —OCO—, —OCO—O—, —S—CO— or —CO—S— in such a manner that oxygen atoms are not inked directly to one another, Q3 is halogen, a cyano group or an alkyl or alkoxy group with 1 to 4 C atoms, wherein Q$^3$ is different from Q$^2$.

Preferred chiral groups R are 2-butyl (=I-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa4-methylpentyl, 4-methylhexyl, 2-nonyl, 2-decyl, 2-dodecyl, 6-methoxyoctoxy, 6-methyloctoxy, 6-methyloctanoyloxy, 5-methyl heptyloxycarbonyl, 2-methyl butyryloxy, 3-methylvaleroyloxy, 4-methylhexanoyloxy, 2-chlorpropionyloxy, 2-chloro-3-methylbutyryloxy, 2-chloro4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, I -propoxypropyl-2-oxy, 1 -butoxypropyl-2-oxy, 2-fluorooctyloxy, 2-fluorodecyloxy for example.

In addition, chiral compounds of the formula I containing an achiral branched group R may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

A particularly preferred embodiment of the present invention is related to polymerizable compounds of formula I, wherein at least one of the groups R$^1$ to R$^4$ comprises a terminal polymerizable group P.

Of these compounds, especially preferred are those of formulae Ia to Ip, wherein one, two, three or four, in particular one or two groups R are denoting P—(Sp—X)$_n$—. Very particularly preferred are compounds wherein the groups R denoting P—(Sp—X)$_n$— are adjacent to a mesogenic group MG.

Of the preferred compounds described above in particular preferred are those wherein n is 1.

Further preferred are compounds comprising at least one group R denoting P-(Sp-X)$_n$- wherein n is 0 and at least one group R denoting P-(Sp-X)$_n$- wherein n is 1.

Also preferred are compounds wherein at least one, in particular one or two, of R$^1$, R$^2$, R$^3$, and R$^4$ are denoting -(Sp-X)$_n$MG-R wherein n is 0.

The polymerizable group P is preferably selected from WHC

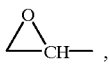

$CH_2=CW-COO-$, $WCH=CH-(O)_k-$, and $CH_2=CH-Phenyl-(O)_k-$, with W being H, $CH_3$ or Cl and k being 0 or 1.

P is preferably a vinyl group, an acrylate group, a methacrylate group, a propenyl ether group or an epoxy group, especially preferably an acrylate or a methacrylate group.

In the event that one or more groups $R^1$ to $R^4$ are denoting $-(Sp-X)_n-$ MG-R wherein R is $P-(Sp-X)_n-$, the two spacer groups Sp on both sides of the mesogenic group MG can be identical or different.

As for the spacer group Sp in formula I all groups can be used that are known for this purpose to the skilled in the art. The spacer group Sp is preferably a linear or branched alkylene group having 1 to 20 C atoms, in particular 1 to 12 C atoms, in which, in addition, one or more nonadjacent $CH_2$ groups may be replaced by $-O-$, $-S-$, $-NH-$, $-N(CH_3)-$, $-CO-$, $-O-CO-$, $-S-CO-$, $-O-COO-$, $-CO-S-$, $-CO-O-$, $-CH(halogen)-$, $-CH(CN)-$, $-CH=CH-$ or $-C\equiv C-$.

Typical spacer groups are for example $-(CH_2)_o-$, $-(CH_2CH_2O)_r-CH_2CH_2-$, $-CH_2CH_2-S-CH_2CH_2-$ or $-CH_2CH_2-NH-CH_2CH_2-$, with o being an integer from 2 to 12 and r being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Especially preferred are inventive chiral compounds of formula I wherein Sp is alkylene or alkyleneoxy group with 2 to 6 C atoms. Straight-chain alkylene or alkyleneoxy groups are especially preferred. In another preferred embodiment of the invention the chiral compounds of formula I comprise at least one spacer group Sp that is a chiral group of the formula IV:

IV

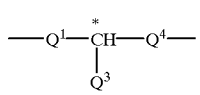

wherein
$Q^1$ and $Q^3$ have the meanings given in formula III, and
$Q^4$ is an alkylene or alkylene-oxy group with 1 to 10 C atoms or a single bond, being different from $Q^1$.

The chiral structure element in formula I can be obtained by osmium catalyzed asymmetric dihydroxylation of the corresponding olefin in the presence of $[DHQD]_2PHAL$ (hydroquinidine 1,4-phthalazinediyl diether) or $[DHQ]_2PHAL$ (hydroquinine 1,4-phthalazinediyl diether, both commercially available from Aldrich), in analogy to the methods described, e.g., by K. B. Sharpless et al., *J. Org. Chem.* 57, 1992, 2768–2771 and S. Torii et al., *J. Org. Chem.* 61, 1996, 3055–3060. According to this method both the R,S and the S,R enantiomer can be synthesized.

Especially preferred are chiral compounds of formula I wherein the two chiral C atoms exhibit an S,R- or an R,S-configuration.

In particular, the inventive chiral compounds can be synthesized according to or in analogy to reaction scheme 1.

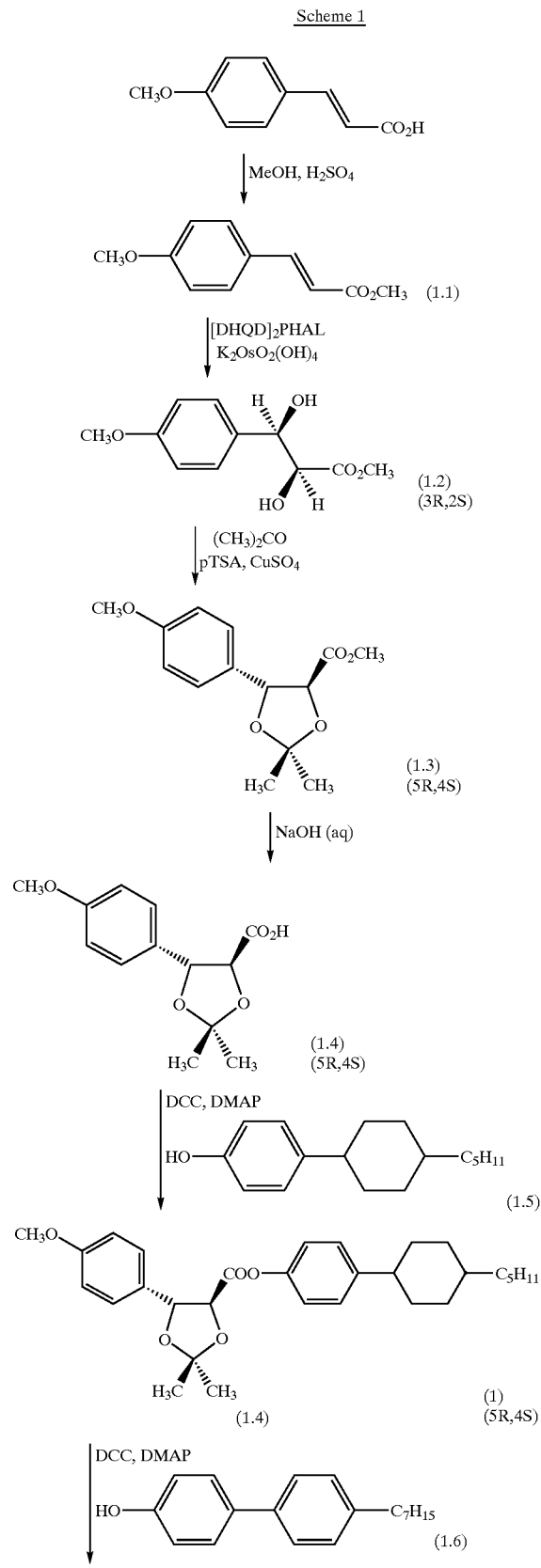

Scheme 1

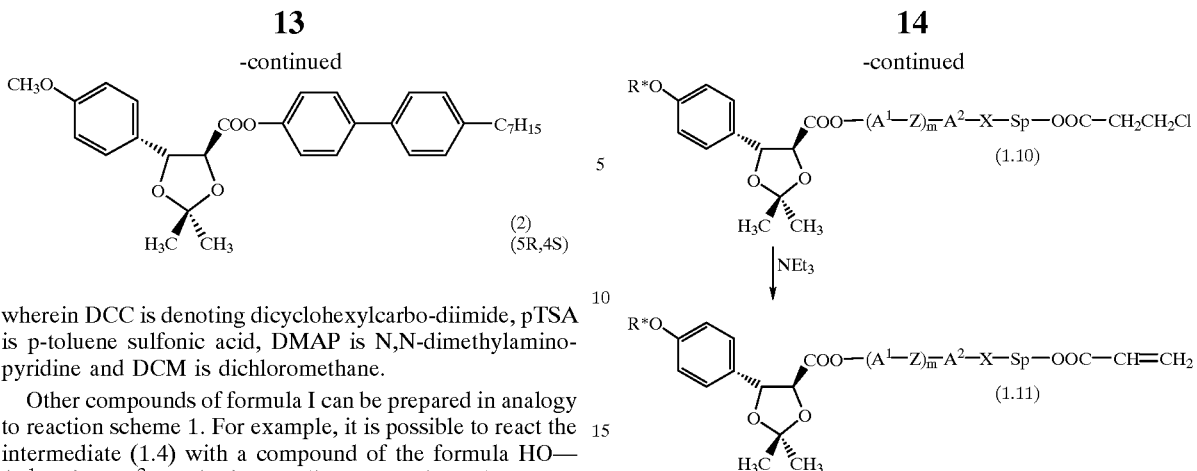

wherein DCC is denoting dicyclohexylcarbo-diimide, pTSA is p-toluene sulfonic acid, DMAP is N,N-dimethylamino-pyridine and DCM is dichloromethane.

Other compounds of formula I can be prepared in analogy to reaction scheme 1. For example, it is possible to react the intermediate (1.4) with a compound of the formula HO—$(A^1—Z)_m—A^2$—R (1.7) according to reaction scheme 2.

Scheme 2

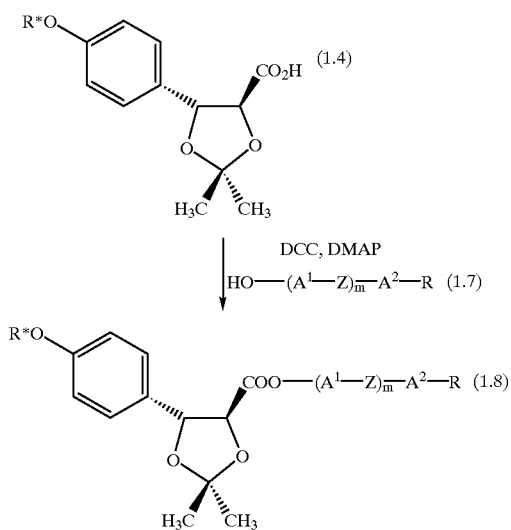

wherein R* has one of the meanings of R in formula I*, R has the meaning of formula I* and $A^1, A^2$, Z and m have the meanings of formula II.

It is further possible to prepare polymerizable compounds of formula I for example by reacting the intermediate (1.4) with a compound of formula HO—$(A^1—Z)_m—A^2$—X—Sp—OOC—CH$_2$CH$_2$Cl (1.9), and treating the resulting intermediate with NEt$_3$ according to reaction scheme 3.

Scheme 3

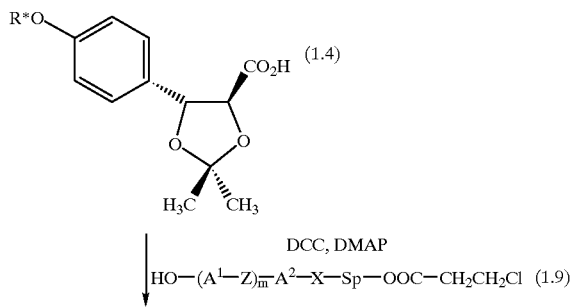

wherein R* has the meaning given above, X has the meaning given in formula I, Sp has the meaning given in formula I* and $A^1, A^2$, Z and m have the meanings given in formula II.

Other methods of preparation can be taken from the examples.

The inventive chiral compounds can be used in a liquid crystal mixture for displays exhibiting a twisted molecular structure of the liquid crystal matrix like, for example, supertwisted or active matrix liquid crystal displays, or in displays comprising a liquid crystal mixture with a chiral liquid crystalline phase, like for example chiral smectic or chiral nematic (cholesteric) mixtures for ferroelectric displays or cholesteric displays.

Thus, another object of the invention is a liquid crystalline mixture comprising at least one chiral compound of formula I.

Yet another object of the invention are cholesteric liquid crystal displays comprising cholesteric liquid crystalline media containing at least one chiral compound of formula I.

The inventive chiral compounds of formula I exhibit high values of the HTP. Thus liquid crystalline mixtures with a high helical twist, i.e. a short cholesteric pitch, can be prepared by using the inventive compounds, or otherwise a liquid crystalline mixture with a moderate helical twist can be achieved already when using the inventive compounds as dopants in low amounts.

The high HTP values of the inventive compounds makes them also suitable to be used in combination with other compounds for the temperature compensation of the properties of liquid crystal mixtures, such as the cholesteric pitch, and of the properties of displays, e.g., such as the threshold voltage.

In a preferred embodiment of the invention the chiral compounds show a strong temperature dependence of the HTP in nematic liquid crystal mixtures.

The inventive compounds are furthermore advantageous because they are affecting the physical properties of the liquid crystalline mixture only to a minor extent.

Thus, when admixing the chiral compounds of formula I for example to a liquid crystalline mixture with positive dielectric anisotrophy that is to be used in a liquid crystal display, As is only slightly reduced and the viscosity of the liquid crystalline mixture is increased only to a smal extent. This leads to lower voltages and improved switching times of the display when compared to a display comprising conventional dopants.

In a particularly preferred embodiment of the invention the chiral compounds show a small temperature dependence of the HTP in nematic liquid crystal mixtures.

The liquid crystalline mixture according to the invention comprises preferably 0.001 to 15%, in particular 0.01 to 8% and very particularly preferably 0.1 to 5% by weight of chiral compounds of formula I.

The liquid crystalline mixture according to the invention preferably comprises 1 to 3 chiral compounds of formula I.

For temperature compensation applications as described above the liquid crystalline mixture preferably contains a chiral component which contains at least one chiral compound of formula I.

In a preferred embodiment of the invention the liquid crystalline mixture contains 2 to 25, preferably 3 to 15 compounds, at least one of which is a chiral compound of formula I. The other compounds are preferably low molecular weight liquid crystalline compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohlhexyl pyrimidines, phenyl- or cyclohexylpyridines, phenyl- or cyclohexylpyridazines, phenyl- or cyclohexyldioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)ethanes, 1-cyclohexyl-2-biphenyl-ethanes, 1-phenyl2-cyclohexylphenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystalline mixture of this preferred embodiment is based on the achiral compounds of this type.

The most important compounds that are posssible as components of these liquid crystalline mixtures can be characterized by the following formula

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, -B-Phe- and -B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and B is 2-(trans-1,4-cyclohexyl)ethyl, pyrimidinie-2,5-diyl, pyridine-2,5-diyl or 1,3-dioxane-2,5-diyl.

G' in these compounds is selected from the following bivalent groups

—CH=CH—, —N(O)N—, —CH=CY—, —CH=N (O)—, —C≡C—, —CH$_2$—CH$_2$—, —CO—O—, —CH$_2$—O—, —CO—S—, —CH$_2$—S—, —CH=N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is 2 to 9, preferably 2 to 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

The inventive compounds are in particular useful for anisotropic polymer gels and for low molar mass or polymerizable or polymerized cholesteric liquid crystalline mixtures for cholesteric displays, such as for example phase change displays or surface stabilized or polymer stabilized cholesteric texture displays (SSCT, PSCT).

A further advantage of the chiral compounds according to the invention is that cholesteric liquid crystalline mixtures or materials comprising these compounds exhibit a low temperature dependence of the reflection wavelength $d\lambda/dT$ (T=temperature, $\lambda$=reflection wavelength maximum).

Cholesteric displays are described for example in WO 92/19695, WO 93/23496, U.S Pat. Nos. 5,453,863 or 5,493,430, wherein the entire disclosures of these documents are incorporated into this application by reference.

Furthermore, anisotropic polymer gels and displays comprising them are disclosed for example in DE 195 04 224 and GB 2 279 659.

It has been found that PSCT displays comprising the inventive compounds have reduced response times, lower voltages and improved contrast compared to displays comprising conventional dopants, like, e.g., R 811 or CB 15, that are commercially available by Merck KGaA (Darmstadt, Germany). For example, PSCT displays in which the conventional dopants are replaced by chiral compounds according to the present invention can show reduced switching time.

Cholesteric films made by using the inventive compounds instead of prior art dopants show improved brightness, leading to a better contrast between the colored planar texture and the almost clear focal conic state which is made black using a black backplate.

The inventive chiral compounds and polymerizable liquid crystalline mixtures comprising these compounds are also particularly useful for the preparation of anisotropic polymer films with a chiral liquid crystalline phase, such as cholesteric or chiral smectic polymer films, in particular films that exhibit helically twisted molecular structure with uniform planar orientation, i.e., wherein the helical axis is oriented perpendicular to the plane of the film.

For example, oriented cholesteric polymer films can be used as broad waveband reflective polarizers, as described e.g. in EP 0 606 940, as color filters, for security markings, or for the preparation of liquid crystal pigments. I. Heynderickx and D.J. Broer in Mol. Cryst. Liq. Cryst. 203, 113–126 (1991) describe crosslinked cholesteric polymer films that are made of liquid crystalline diacrylates and contain a low molecular weight chiral dopant.

It has been found that cholesteric polymer films made by using the inventive chiral compounds are brighter compared to films comprising dopants of prior art like, e.g., R 811 or CB 15 as mentioned above.

For the preparation of anisotropic polymer gels or oriented polymer films, the liquid crystalline mixture should comprise at least one polymerizable compound, preferably a polymerizable mesogenic compound, in additon to chiral compounds of formula I.

Thus, another object of the invention are polymerizable liquid go crystalline mixtures comprising at least one chiral compound of formula I and at least one polymerizable mesogenic compound.

Suitable polymerizable mesogenic compounds are described for example in WO 93/22397; EP 0 261 712; DE 19504224, DE 4408171 or DE 4405316. The compounds disclosed in these documents, however, are to be regarded merely as examples that shall not limit the scope of this invention.

Furthermore, typical examples representing polymerizable mesogenic compounds are shown in the following list of compounds, which should, however, be taken only as illustrative and is in no way intended to restrict, but instead to explain the present invention:

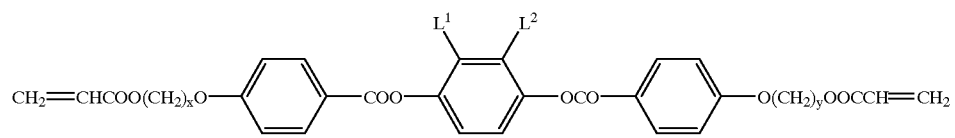
(V1)

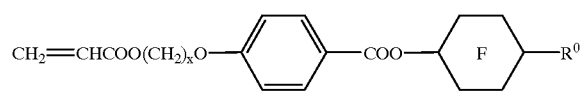
(V2)

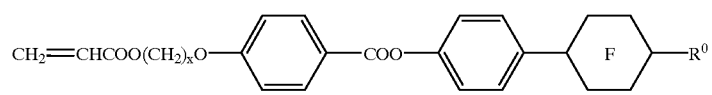
(V3)

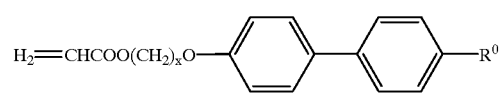
(V4)

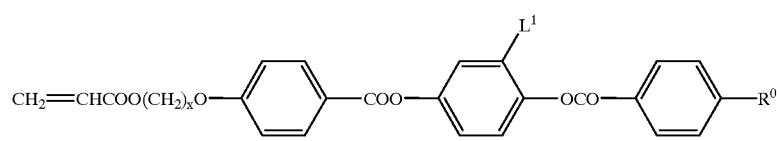
(V5)

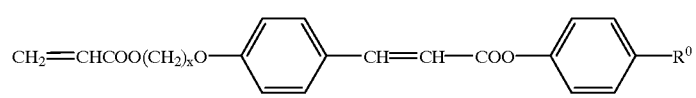
(V6)

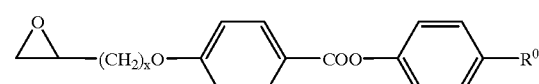
(V7)

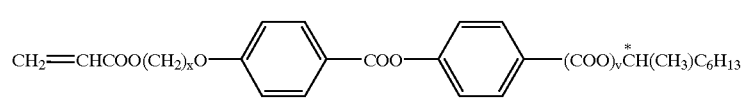
(V8)

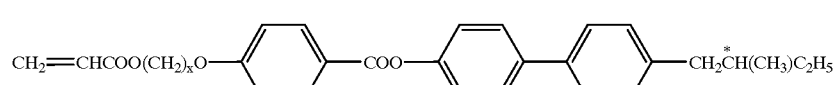
(V9)

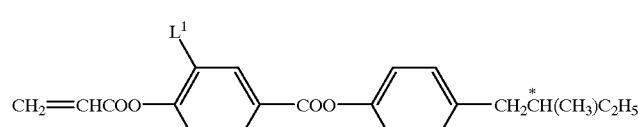
(V10)

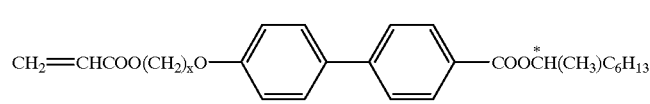
(V11)

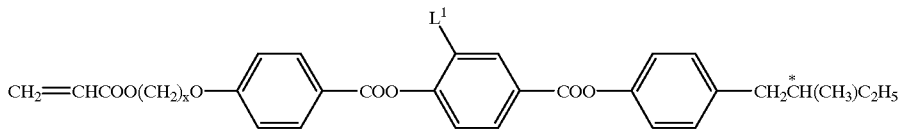
(V12)

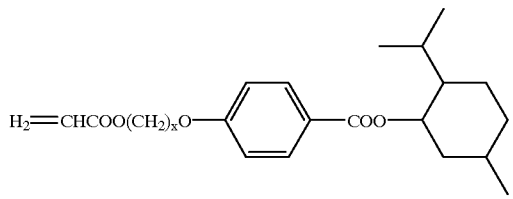
(V13)

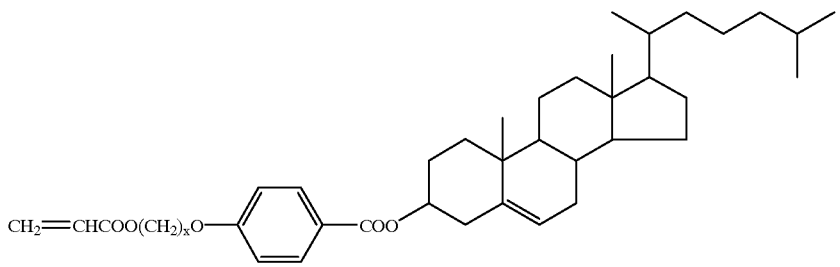
(V14)

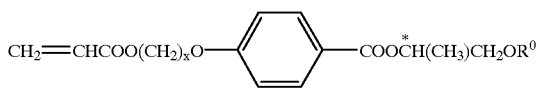
(V15)

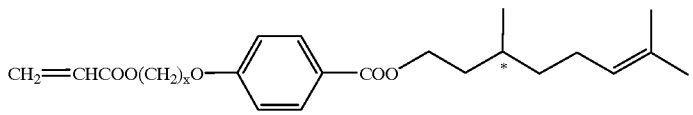
(V16)

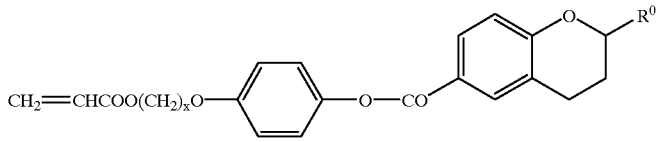
(V17)

In these compounds x and y are each independently 1 to 12; v is 0 or 1, F is a 1,4-phenylene or 1,4-cyclohexylene group, $R^0$ is halogen, cyano or an optionally halogenated alkyl or alkoxy group with 1 to 12 C atoms and $L^1$ and $L^2$ are each independently H, F, Cl, CN, or an optionally halogenated alkyl, alkoxy or alkoxycarbonyl group with 1 to 7 C atoms.

The polymerizable mesogenic compounds of formula V1–V17 can be prepared by methods which are known per se and which are described in the documents cited above and, for example, in standard works of organic chemistry such as, for example, Houben-Weyl, Methoden der organischen Chemie, Thieme-Verlag, Stuttgart.

The polymerizable mesogenic compounds of formula V1–V17 can be mono- or bifunctional, i.e. they can have one or two polymerizable functional groups.

In a preferred embodiment of the invention the polymerizable liquid crystalline mixtures comprise at least one inventive chiral compound, at least one monofunctional and at least one bifunctional polymerizable compound of formulae V1–V17.

In another preferred embodiment the polymerizable liquid crystalline mixtures comprise at least one inventive chiral compound and at least two monofunctional compounds of formulae V1–V17.

It is also possible that the polymerizable liquid crystalline mixture comprises one or more polymerizable compounds of formula I instead of or in addition to the polymerizable mesogenic compounds of formulae V1–V17.

Thus, another object of the invention are polymerizable liquid crystalline mixtures comprising at least one chiral compound of formula I comprising at least one polymerizable functional group.

In a preferred embodiment the polymerizable liquid crystalline mixtures comprise at least one chiral compound of formula I comprising one polymerizable functional group.

In another preferred embodiment the polymerizable liquid crystalline mixtures comprise at least one chiral compound of formula I comprising two polymerizable functional groups.

Another object of the invention is an anisotropic polymer film with an oriented chiral liquid crystalline phase obtainable by (co)polymerizing a liquid crystalline mixture comprising at least one chiral compound of formula I and at least one polymerizable mesogenic compound preferably selected of formula V1–V17 and/or at least one polymerizable chiral compound of formula I.

To prepare anisotropic polymer film with a chiral liquid crystalline phase with uniform orientation the inventive liquid crystalline mixtures, for example, are coated onto a substrate, aligned and polymerized in situ by exposing them to heat or actinic radiation. Alignment and curing are preferably carried out in the liquid crystalline phase of the liquid crystalline mixtures.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like, e.g., a UV laser, an IR laser or a visible laser.

For example, when polymerizing by means of UV light, a photoinitiator can be used that decomposes under UV irradiation to produce free radicals or ions that start the polymerization reaction.

It is also possible to use a cationic photoinitiator, when curing reactive mesogens with for example vinyl and epoxide reactive groups, that photocures with cations instead of free radicals.

As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used.

Preferably the polymerizable liquid crystalline mixtures comprising polymerizable chiral compounds of formula I and/or polymerizable mesogenic compounds of formulae V1–V17 additionally comprise 0.01 to 10%, in particular 0.05 to 8%, very preferably 0.1 to 5% by weight of a photoinitiator, especially preferably a UV-photoinitiator.

In a preferred embodiment of the invention the polymerization of the polymerizable mesogenic material is carried out under an atmosphere of inert gas, preferably under a nitrogen atmosphere.

As a substrate for example a glass or quarz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization.

Isotropic or birefringent substrates can be used. In case the substrate is not removed from the polymerized film after polymerization, preferably isotropic substrates are used.

Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

In a preferred embodiment of the present invention, the inventive mixture of the polymerizable liquid crystalline mixture comprising a chiral compound of formula I is coated as a thin layer on a substrate or between substrate, and is preferably aligned in its chiral mesophase, eg. the cholesteric or chiral smectic phase, to give a planar orientation, i.e. an orientation so that the axis of the molecular helix extends transversely to the layer.

A planar orientation can be achieved for example by shearing the mixture, e.g. by means of a doctor blade. It is also possible to apply an alignment layer, for example a layer of rubbed polyimide or sputtered $SiO_x$, on top of at least one of the substrates.

In another preferred embodiment, a second substrate is put on top of the coated material. In this case, the shearing caused by putting together the two substrates is sufficient to give good alignment.

It is also possible to apply an electric or magnetic field to the coated mixture.

In some cases it is of advantage to apply a second substrate not only to aid alignment of the polymerizable mixture but also to exclude oxygen that may inhibit the polymerization. Alternatively the curing can be carried out under an atmosphere of inert gas. However, curing in air is also possible using suitable photoinitiators and high lamp power. When using a cationic photoinifiator oxygen exclusion most often is not needed, but water should be excluded.

A detailed description of the in situ polymerization of polymerizable mesogenic compounds can be found in D. J. Broer et al., Makromolekulare Chemie 190, 2255 (1989).

The inventive polymerizable liquid crystalline mixtures comprise preferably 0.001 to 15%, in particular 0.01 to 8% and very particularly preferably 0.1 to 5% by weight of non-polymerizable chiral compounds of formula I.

Polymerizable liquid crystalline mixtures are preferred that comprise 1 to 3 chiral compounds of formula I.

If polymerizable chiral compounds of formula I are present in the inventive polymerizable liquid crystalline mixtures, these compounds can also be used in the inventive polymerizable liquid crystalline mixtures in higher amounts than given above for the non-polymerizable chiral compounds of formula I.

In a preferred embodiment of the present invention the polymerizable liquid crystalline mixtures are comprising 1 to 80% by weight, preferably 2 to 60%, in particular 5 to 40% by weight of a polymerizable chiral compound of formula I comprising at least one polymerizable functional group.

Of the polymerizable liquid crystalline mixtures comprising one or more polymerizable chiral compounds of formula I with one polymerizable functional groups (=monofunctional compounds), particularly preferred are those comprising 1 to 60%, in particular 2 to 45%, very preferably 3 to 35% by weight of a polymerizable chiral monofunctional compound of formula I.

Of the polymerizable liquid crystalline mixtures comprising one or more polymerizable chiral compounds of formula I with two polymerizable functional groups (=bifunctional compounds), particularly preferred are those comprising 1 to 50%, in particular 2 to 35%, very preferably 3 to 25% by weight of a polymerizable chiral bifunctional compound of formula I.

The inventive polymerizable liquid crystalline mixtures can additionally comprise one or more other suitable components, such as, for example, catalysts, sensitizers, stabilizers, co-reacting monomers or surface-active compounds.

In a preferred embodiment of the invention, the inventive polymerizable liquid crystalline mixture comprises a stabilizer that is used to prevent undesired spontaneous polymerization for example during storage of the composition. As stabilizers in principal all compounds can be used that are known to the skilled in the art for this purpose. These compounds are commercially available in a broad variety. Typical examples for stabilizers are 4-ethoxyphenol or butylated hydroxytoluene (BHT).

It is also possible, in order to increase crosslinking of the polymers, to add up to 20% of a non mesogenic compound with two or more polymerizable functional groups to the polymerizable composition alternatively or additionally to the multifunctional polymerizable mesogenic compounds.

Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Polymerization of inventive compositions comprising compounds with only one polymerizable functional group leads to linear polymers, whereas in the presence of compounds with more than one polymerizable functional group crosslinked polymers are obtained.

For the preparation of anisotropic polymer gels, the liquid crystalline mixtures can be polymerized in situ as described above, however, in this case alignment of the polymerizable mixture is not necessary.

The inventive chiral compounds of formula I can also be used for the prepration of thermochromic liquid crystalline mixtures. Such mixtures are characterized in that they exhibit a chiral liquid crystalline phase or chiral mesophase, like e.g. a chiral smectic phase or a chiral nematic (=cholesteric) phase, with a helically twisted molecular structure that shows selective reflection of a specific waveband of light, wherein the pitch of the molecular helix and thereby the reflected wavelengths are depending on the temperature.

Especially preferred are inventive liquid crystalline mixtures with thermochromic behaviour that exhibit a cholesteric phase. Of these preferred compositions, further preferred are compositions that exhibit a cholesteric phase and a smectic phase, most preferably a chiral smectic phase, at temperatures below the temperature range of the cholesteric phase. The inventive liquid crystalline mixtures exhibiting thermochromic behaviour can be polymerizable or non-polymerizable.

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to ist fullest extent. The following examples are, therefore, to be construed as merely illustrative and not limitative of the remainder of the disclosure in any way whatsoever.

In the foregoing and in the following examples, unless otherwise indicated, all temperatures are set forth uncorrected in degrees Celsius and all parts and percentages are by weight.

The values of the helical twisting power HTP of a chiral compound in a liquid crystalline host are given according to the equation HTP=$(p*c)^{-1}$ in $\mu m^{-1}$, wherein p is the pitch of the molecular helix, given in $\mu m$, and c is the concentration by weight of the chiral compound in the host given in relative values (thus, e.g. a concentration of 1% by weight is corresponding to a value of c of 0.01).

The following abbreviations are used to illustrate the liquid crystalline phase behavior of the compounds:

K=crystalline; N=nematic; S=smectic; Ch=cholesteric; I=isotropic. The numbers between these symbols indicate the phase transition temperatures in degree Celsius.

In addition, the following abbreviations are used
DCC=dicyclohexylcarbodiimide
DCM=dichloromethane
HTP=helical twisting power
mp=melting point

EXAMPLES

Example 1

Compound (1) was prepared according to reaction scheme 1

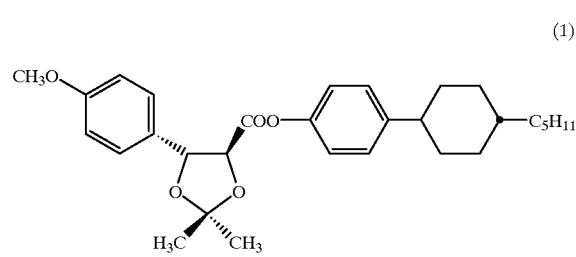

(1)

(E)-3-(4-methoxyphenyl)-2-propenoate (1.1)

Trans-Methoxycinnamic acid (17.8 g, 100 mmol), sulphuric acid (2 ml) and methanol (200 ml) were stirred under reflux for 2 hours. The mixture was cooled, concentrated in vacuo, white crystals precipitated and these were isolated by vacuum filtration to give methyl (E)-3-(4-methoxyphenyl)-2-propenoate (16.1 g, 84%). $^1$-NMR gave the expected signals.

3R,2S-Methyl 2,3-dihydroxy-3-(4-methoxyphenyl) propanoate (1.2)

[DHQD]$_2$PHAL (54.5 mg, 0.25 mol %), methyl (E)-3-(4-methoxyphenyl)-2-propenoate (5.38 g, 28 mmol), N-methyl morpholine N-oxide (60% aqueous solution, 7.0 ml) and tert-butanol (11.2 ml) were charged to a 100 ml 3-neck flask and stirred at room temperature. Potassium osmate (VI) dihydrate (21.4 mg, 0.2 mol %) was added portionwise and the reaction was stirred at room temperature. The reaction procedure was monitored by HPLC. After 17 hours, Tiron (200 mg) was added to quench the reaction, followed by water (50 ml). The mixture was allowed to stir for one hour, ethyl acetate (50 ml) was added to the mixture and the resultant two layers were vigorously stirred for 30 minutes. The organic phase was removed and washed with water, dried (Na$_2$SO$_4$) and evaporated to dryness on a rotary evaporator. The product was purified by flash column chromatography using DCM: ethyl acetate (3:2) as eluant. Evaporation of the appropriate fractions gave methyl 2,3-dihydroxy-3-(4-methoxyphenyl)propanoate as a white crystalline solid (3.2 g, 62%). mp. 108° C., [α]$_D$=−1.2° (THF, conc.=0.01306 22° C.). $^1$H-NMR was in accordance with expected signals.

Methyl 5-(4-methoxyphenyl)-2,2-dimethyl -1,3-dioxolane 4-carboxylate (1.3)

Methyl 2,3-dihydroxy-3-(4-methoxyphenyl)propanoate (3.5 g, 15.5 mmol), copper sulphate anhydrous (4.3 g, 27 mmol, 1.8 equiv.) and acetone (40 ml, excess) were stirred in the presence of a catalytic amount of para-toluene sulphonic acid at 35° C. After 16 hours, the copper sulphate was removed by filtration, and the filtrate was removed and evaporated to dryness on a rotary evaporator. The product was purified by flash column chromatography using DCM as eluant. Evaporation of the appropriate fractions left methyl 5-(4-methoxyphenyl)-2,2-dimethyl -1,3-dioxolane 4-carboxylate as a clear, colourless oil (4.0 g, 96%). [a]$_D$=+37.4° (THF, conc.=0.01712, 20° C). $^1$H-NMR was in accordance with expected signals.

(5R, 4S)-5-(4-methoxyphenyl)2,2-dimethyl-1,3-dioxolane-4-carboxylic acid (1.4)

Methyl 5-(4-methoxyphenyl)-2,2-dimethyl-1,3-dioxolane 4-carboxylate (2.0 g, 7.5 mmol) and aqueous sodium hydroxide solution (0.36 g in 20 ml) and industrial methylated spirits (20 ml) were stirred at 80° C. for 3 hours. The mixture was cooled to room temperature, neutralised with dilute hydrochloric acid and concentrated in vacuo. The product was extracted with DCM, dried over NaSO$_4$ and evaporated to dryness to leave (5R,4S)-5-(4-methoxyphenyl)2,2-dimethyl-1,3-dioxolane-4-carboxylic acid as a colourless oil (1.7 g, 90%). $^1$H-NMR was in accordance with expected signals. I.R. showed expected peaks.

(5R,4S)-5-(4-methoxyphenyl)2,2-dimethyl-1,3-dioxolane-4-carbonyloxycyclohexyl-4-phenyl-4'-pentane (1)

(5R,4S)-5-(4-Methoxyphenyl)2,2-dimethyl-1,3-dioxolane-4-carboxylic acid (1.6 g, 6.3 mmol), DCC (1.44 g, 7.0 mmol), 4-(4'-pentylcylohexyl)phenol (1.5) (1.55g, 6.3 mmol) and a catalytic amount of dimethylamino pyridine were stirred at room temperature in dichloromethane (40 ml). After 3 hours, the precipitate of dicyclohexyl urea was removed by filtration, the filtrate was washed with water, dried (Na$_2$SO$_4$) and evaporated to dryness. The product was purified by flash column chromatography using DCM as eluant to leave (5R,4S)-5-(4-methoxyphenyl)2,2-dimethyl-1,3-dioxolane4-carbonyloxycyclohexyl-4-phenyl-4'-pentane (1), a clear, colourless oil on evaporation of the appropriate fractions. Yield=1.6 g, 53%. mp. 56° C. [a]$_D$32 +89.9° (THF, conc.=0.01124, 25° C.). $^1$H-NMR was in accordance with expected signals.

Example 2

Compound (2) was prepared according to reaction scheme 1.

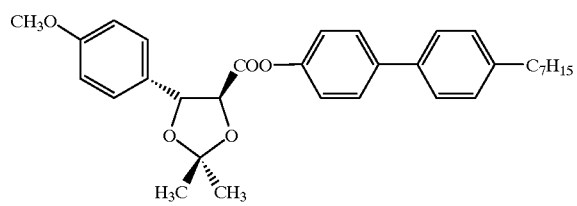

(2)

(5R,4S)-5-(4-Methoxyphenyl)2,2-dimethyl-1,3-dioxolane-4-carboxylic acid (1.4) (0.8 g, 3.2 mmol), DCC (0.7 g, 3.5 mmol), 4-(4'-heptylphenyl)phenol (1.6) (0.8 g, 3.2 mmol) and a catalytic amount of dimethylamino pyridine were stirred at room temperature in dichloromethane (40 ml). After 3 hours, the precipitate of dicyclohexyl urea was removed by filtration, the filtrate was washed with water, dried (Na$_2$SO$_4$) and evaporated to dryness. The product was purified by flash column chromatography using DCM as eluant to leave (5R,4S)-5-(4-methoxyphenyl)2,2-dimethyl-1,3-dioxolane-4-carbonyloxyphenyl-4-phenylheptane (2) as a clear, colourless oil on evaporation of the appropriate fractions. Yield=0.8 g, 50%. Mp. 60° C. [a]$_D$=+103.70 (THF, conc.=0.01326, 25° C.). $^1$H NMR was in accordance with expected signals.

Example 3

Compound (3) was prepared according to reaction scheme 1.

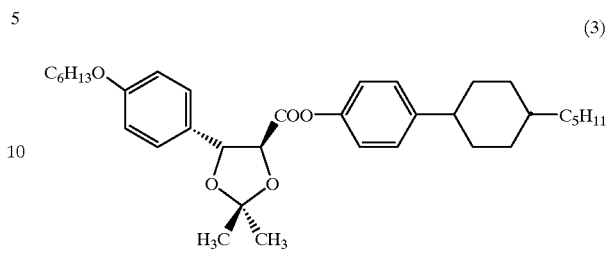

(3)

The trans methyl 4-alkoxycinnamate (homologue of compound 1.1) in the first step was prepared by Williamson etherification of trans methyl 4-hydroxycinnamate with the corresponding bromoalkane.

Methyl (E)-3-(4-hexyloxyphenyl)-2-propenoate (3.1)

Trans methyl 4-hydroxycinnamate (20.0 g, 11.2 mmol), 1-bromohexane (18.5 g, 112 mmol) and potassium carbonate (16.6 g, 120 mmol) were stirred under reflux in butanone. The mixture was allowed to cool after 16 hours, evaporated to dryness and the residue was partitioned between DCM and water. The DCM layer was removed and dried (Na$_2$SO$_4$) and evaporated to leave a yellow solid methyl (E)-3-(4-hexyloxyphenyl)-2-propenoate which was recrystallized from petroleum. Yield=20.0 g, 71%.

Methyl 2,3-dihydroxy-3-(4-hexyloxynhenyl)propanoate (3.2)

Synthesis and purification were carried out as described in example 1. Methyl 2,3-dihydroxy-3-(4-hexyloxyphenyl)propanoate was obtained as a colourless oil which crystallized on standing (3.4 g, 62%). $^1$H-NMR was in accordance with expected signals.

(5R, 4S)-methyl5-(4-hexyloxyphenyl)-2,2-dimethyl-1,3-dioxolane 4-carboxylate (3.3)

Synthesis and purification were carried out as described in example 1. (5R,4S)-methyl 5-(4-methoxyphenyl)-2,2-dimethyl -1,3-dioxolane 4-carboxylate was obtained as an oil (2.5 g, 69%). [α]$_D$=36.5° (THF, conc.=0.01768, 19° C.). $^1$H-NMR was in accordance with expected signals. The HTP was 2 $\mu$m$^{-1}$, measured in the commercially available nematic host mixture BL 087 (from Merck Ltd., Poole, UK) at a concentration of 6.34% by weight.

(5R,4S)-5-(4-hexyloxyphenyl)2,2-dimethyl-1,3-dioxolane-4-carboxylic acid (3.4)

Synthesis and purification were carried out as described in example 1. (5R,4S)-5-(4-hexyloxyphenyl)2,2-dimethyl-1,3-dioxolane-4-carboxylic acid was obtained as a yellow oil (1.7 g, 90%). $^1$H-NMR and I.R. spectra were in accordance with expected signals. [a]$_D$=+22.50 (THF, conc.=0.01731, 19° C.).

(5R,4S5-(4-hexyloxyphenyl)2,2-dimethyl-1,3-dioxolane-4-carbonyloxycyclohexyl-4-phenyl-4'-pentane (3)

Synthesis and purification were carried out as described in example 1. (5R,4S)-5-(4-methoxyphenyl)2,2-dimethyl-1,3-dioxolane-4-carbonyloxycyclohexyl-4-phenyl-4'-pentane (3) was obtained as a clear oil. Yield=59%. [a]$_D$=+112.8° (THF, conc.=0.01037, 22° C). $^1$H-NMR was in accordance with expected signals.

The HTP of (3) was 14.9 $\mu$m$^{-1}$, measured in the commercially available nematic host mixture BL 087 (from Merck Ltd., Poole, UK) at a concentration of 5.11% by weight.

The entire disclosure of all applications, patents and publications, cited above, and of corresponding European patent application No. 98118646.3, filed Oct. 2, 1998, is hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications, of the invention to adapt it to various conditions and usages.

What is claimed is:

1. A chiral compound of formula I

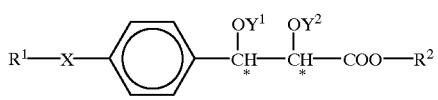    I wherein

C is a chiral carbon atom;
*

$Y^1$ is -Y-$R^3$ and $Y^2$ is -Y-$R^4$, or alternatively $Y^1$ and $Y^2$ together are —CO— or —C($XR^3$)($XR^4$)—;

$R^1$, $R^2$, $R^3$ and $R^4$ are independently of each other H, CN, halogen, or an aromatic, aliphatic or araliphatic group with up to 50 C atoms;

X is in each case independently —O—, —S—, —CO—, —COO—, —OCO—, —OCO—O, —CO—NH—, —NH—CO—, —OCH$_2$—, —CH$_2$O—, —CH=CH—, —C≡C—, —SCH$_2$—, —CH$_2$S—, —CH=CH—COO—, —OOC—CH=CH— or a single bond; and Y is in each case independently —CO—, —COO—, —CO—NH—, —CO—CH=CH— or a single bond wherein a) if $Y^1$ and $R^1$-X are each H and $Y^2$ is phenyl, then $R^2$ is not H or CH$_3$; and b) if $Y^1$ is Y-$R^3$ and $Y^2$ is Y-$R^4$, then Y—$R^3$ and Y-$R^4$ are not both H, or c) when $Y^1$ and $Y^2$ together are —CO— or —C($XR^3$)($XR^4$)—, then at least one of $R^1$, $R^2$, $R^3$ and $R^4$ is of formula I*

-(Sp-X)$_n$-MG-R    I* wherein

Sp is in each case independently a spacer group with 1 to 20 C atoms;

n is 0 or 1;

MG is a bicyclic or tricyclic mesogenic group;

R is in each case independently H, CN, halogen, a straight-chain or branched-chain alkyl having up to 25 C atoms which is unsubstitued, or mono- or polysubstituted by halogen or CN, or a staight-chain or branched-chain alkyl having up to 25 C atoms in which one or more nonadjacent CH$_2$ groups is, in each case independently from one another, replaced by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another and which is unsubstituted, or mono- or polysubstituted by halogen or CN, or R can also be in each case independently P-(Sp-X)$_n$-; and P is a polymerizable group.

2. A chiral compound of formula I

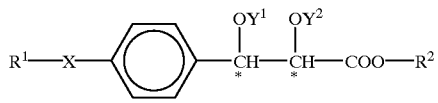    I wherein

C is a chiral carbon atom;
*

$Y^1$ is -Y-$R^3$ and $Y^2$ is -Y-$R^4$, or alternatively $Y^1$ and $Y^2$ together are —CO— or —C($XR^3$)($XR^4$)—;

$R^1$, $R^2$, $R^3$ and $R^4$ are independently of each other H, CN, halogen, or an aromatic, aliphatic or araliphatic group with up to 50 C atoms;

X is in each case independently —O—, —S—, —CO—, —COO—, —OCO—, —OCO—O, —CO—NH—, —NH—CO—, —OCH$_2$—, —CH$_2$O—, —CH=CH—, —C≡C—, —SCH$_2$—, —CH$_2$S—, —CH=CH—COO—, —OOC—CH=CH— or a single bond; and Y is in each case independently —CO—, —COO—, —CO—NH—, —CO—CH=CH— or a single bond wherein at least one of $R^1$, $R^2$, $R^3$ and $R^4$ is of formula I*

-(Sp-X)$_n$-Mg-R    I* wherein

Sp is in each case independently a spacer group with 1 to 20 C atoms;

n is 0 or 1;

MG is a mesogenic group;

R is in each case independently H, CN, halogen, a straight-chain or branched-chain alkyl having up to 25 C atoms which is unsubstitued, or mono- or polysubstituted by halogen or CN, or a straight-chain or branched-chain alkyl having up to 25 C atoms in which one or more nonadjacent CH$_2$ groups is, in each case independently from one another, replaced by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another and which is unsubstituted, or mono- or polysubstituted by halogen or CN, or R can also be in each case independently P-(Sp-X)$_n$-; and P is a polymerizable group.

3. A chiral compound according to claim 2, wherein MG is of formula II.

-(A$^1$-Z)$_m$-A$^2$-    II wherein

Z is —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH, —C≡C— or a single bond:

A$^1$ and A$^2$ are in each case independently a) 1,4-phenylene in which one or more CH groups can, in each case independently, be replaced by N, b) 1,4-cyclohexylene in which one or two non-adjacent CH$_2$ groups can, in each case independently, be replaced by O or S, c) 1,3-dioxolane-4,5-diyl,
d) 1,4-cyclohexenylene, 1,4-bicyclo-(2,2,2)—, octylene, piperidine- 1,4-diyl naphthalene-2,6-diyl, decahydronaphthalene-2,6-diyl, or 1,2,3,4-tetrahydronaphthalene-2,6-diyl, in which radicals (a) to (d) are unsubstituted, or mono- or polysubstituted by halogen, cyano, nitro, or alkyl, alkoxy, alkylcarbonyl or alkoxycarbonyl gruops having 1 to 7 C atoms wherein one or more H atoms may be replaced by F or Cl; and m is 0, 1, 2 or 3.

4. A chiral compound according to claim 1, wherein at least one of $R^1$, $R^2$, $R^3$ and $R^4$ is R wherein R is in each case independently H, CN, halogen or a straight-chain or branched alkyl radical with up to 25 C atoms which is unsubstituted, or mono- or polysubstituted by halogen or CN, and in which one or more nonadjacent $CH_2$ groups can be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or R is in each case independently P—(Sp—X)$_n$;

Sp is in each case independently a spacer group with 1 to 20 C atoms;

n is 0 or 1; and

P is a polymerizable group.

5. A chiral compound according to claim 2, wherein at least one of $R^1$, $R^2$, $R^3$ and $R^4$ is R wherein R is in each case independently H, CN, halogen or a straight-chain or branched alkyl radical with up to 25 C atoms which is unsubstituted, or mono- or polysubstituted by halogen or CN, and in which one or more nonadjacent $CH_2$ groups can be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or R is in each case independently P-(Sp-X)$_n$;

Sp is in each case independently a spacer group with 1 to 20 C atoms;

n is 0 or 1; and

P is a polymerizable group.

6. A chiral compound according to claim 4, wherein R is alkyl having 1 to 12 C atoms or alkoxy having 1 to 12 C atoms.

7. A chiral compound of formula I

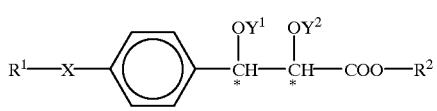

I wherein

C is a chiral atom;

*

$Y^1$ is -Y-$R^3$ and $Y^2$ is -Y-$R^4$, or alternatively $Y^1$ and $Y^2$ together are —CO— or —C($XR^3$)($XR^4$)—;

$R^1$, $R^2$, $R^3$ and $R^4$ are independently of each other H, CN, halogen, or an aromatic, aliphatic or araliphatic group with up to 50 C atoms;

X is in each case independently —O—, —S—, —CO—, —COO—, —OCO—, —OCO—O—O, —CO—NH—, —NH—CO—, —OCH$_2$—, —CH$_2$O—, —CH=CH—, —C≡C—, —SCH$_2$—, —CH$_2$S—, —CH=CH—COO—, —OOC—CH=CH— or a single bond; and Y is in each case independently —CO—, —COO—, —CO—NH—, —CO—CH=CH— or a single bond, wherein at least one of $R^1$, $R^2$, $R^3$ and $R^4$ is wherein R is in each case independently H, CN, halogen or a straight-chain or branched alkyl radical with up to 25 C atoms which is unsubstituted, or mono- or polysubstituted by halogen or CN, and in which one or more nonadjacent $CH_2$ groups can be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or R is in each case independently P-(Sp-X)$_n$;

Sp is in each case independently a spacer group with 1 to 20 C atoms;

n is 0 or 1; and

P is a polymerizable group, and wherein at least one of the groups R is P-(Sp-X)$_n$—.

8. In a liquid crystalline mixture comprising at least two liquid crystal compounds, the improvement wherein said mixture contains at least one compound according to claim 1.

9. A liquid crystalline mixture according to claim 8, further comprising at least one polymerizable mesogenic compound having at least one polymerizable functional group.

10. A chiral linear or crosslinked liquid crystalline polymeric material obtainable by polymerizing a mixture according to claim 9.

11. In a liquid crystal display containing a liquid crystalline mixture, the improvement wherein said liquid crystalline mixture is in accordance with claim 8.

12. A liquid crystal display according to claim 11, wherein said liquid crystalline mixture further comprising at least one polymerizable mesogenic compound having at least one polymerizable functional group.

13. A chiral compound accrding to claim 2, wherein P is WHC

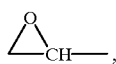, $CH_2$=CW—COO—, WCH=CH—(O)$_k$—, or $CH_2$=CH-Phenyl-(O)$_k$—, W is H, $CH_3$ or Cl, and K is 0 or 1.

14. A chiral compound according to claim 2, wherein Sp is a linear or branched alkylene group having 1 to 20 C atoms, in which, in addition, one or more non-adjacent $CH_2$ groups can be replaced, in each case independently, by —O—, —S—, —NH—, —N($CH_3$)—, —CO—, —O—CO—, —S—CO—, —O—COO—, —CO—S—, —CH(halogen)—, —CH=CH— or —C≡C—.

15. A chiral compound according to claim 2, wherein at least one Sp group is a chiral group of formula IV having up to 20 C atoms

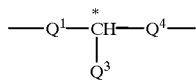

IV wherein
- $Q^1$ is alkylene having 1 to 10 C atoms, alkyleneoxy having 1 to 10 C atoms, or a single bond;
- $Q^3$ is halogen, CN, alkyl having 1 to 4 C atoms, or alkoxy having 1 to 4 C atoms;
- $Q^4$ is alkylene having 1 to 10 atoms, alkyleneoxy having 1 to 10 C atoms, or a single bond, wherein $Q^4$ is different from $Q^1$.

16. A chiral compound according to claim 2, wherein at least one $R^1$, $R^2$, $R^3$ and $R^4$ has a terminal polymerizable group P.

17. In a method for preparing a liquid crystal display selected from STN, TN, AMD-TN, temperature compensation, guest-host, phase change or surface stabilized or polymer stabilized cholestric texure (SSCT, PSCT) displays, said method comprising providing a liquid crystal mixture, the improvement wherein said mixture is one according to claim 8.

18. In a method of preparing an active or passive optical element incorporating a liquid crystal material, the improvement wherein said material is a mixture according to claim 8.

19. In an adhesive composition, cosmetic composition, diagnostic composition, liquid crystal pigment composition, or a synthetic resin composition having isotropic mechanical properties comprising at least one chiral compound, the improvement wherein the composition contains a chiral compound according to claim 1.

20. A liquid crystal display comprising a liquid crystal medium containing a chiral compound, mixture or polymer of claim 1.

21. An SSCT or PSCT display comprising a liquid crystal medium containing a chiral compound, mixture or polymer of claim 1.

22. A passive optical element selected from the group comprising polarizers, compensators, alignment layers, cholesteric filters and holographic elements comprising a chiral compound, mixture or polymer of claim 1.

23. In a liquid cyrstalline mixture comprising at least two liquid crystal compounds, the improvement wherein said mixture contains at least one compound according to formula I

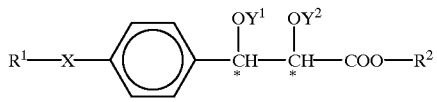

I wherein
- C is a chiral carbon atom;
- *
- $Y^1$ is -Y-$R^3$ and $Y^2$ is -Y-$R^4$, or alternatively $Y^1$ and $Y^2$ together are —CO— or —C($XR^3$)($XR^4$)—;
- $R^1$, $R^2$, $R^3$ and $R^4$ are independently of each other H, CN, halogen, or an aromatic, aliphatic or araliphatic group with up to 50 C atoms;
- X is in each case independently —O—, —S—, —CO—, —COO—, —OCO—, —COC—O—, —CO—NH—, —NH—CO—, —OCH$_2$—, —CH$_2$O—, —CH=CH—, —C≡C—, —SCH$_2$—, —CH$_2$S—, —CH=CH—COO—, —OOC—CH=CH— or a single bond; and
- Y is in each case independently —CO—, —COO—, —CO—NH—, —CO—CH=CH— or a single bond.

24. A liquid crystalline mixture according to claim 23, further comprising at least one polymerizable mesogenic compound having at least one polymerizable functional group.

25. A chiral linear or crosslinked liquid crystalline polymeric material obtainable by polymerizing a mixture according to claim 24.

26. In liquid crystal display containing a liquid crystalline mixture, the improvement wherein said liquid crystalline mixture is in accordance with claim 23.

27. A liquid crystal display according to claim 26, wherein said liquid crystalline mixture further comprising at least one polymerizable mesogenic compound having at least one polymerizable functional group.

28. In a method of preparing an active or passive optical element incorporating a liquid crystal material, the improvement wherein said material is a mixture according to claim 23.

29. A liquid crystal display according to claim 26, wherein said display is an SSCT or PSCT display.

30. In adhesive composition, cosmetic composition, diagnostic composition, liquid crystal pigment composition, or a synthetic resin composition having isotropic mechanical properties comprising at least one chiral compound, the improvement wherein the composition contains a chiral compound according to formula I.

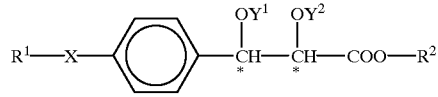

I wherein
- C is a chiral carbon atom;
- *
- is -Y-$R^3$ and $Y^2$ is —Y—$Y^4$, or alternatively $Y^1$ and $Y^2$ together are —CO— or —C($XR^3$)($XR^4$)—;
- $R^1$, $R^2$, $R^3$ and $R^4$ are independently of each other H, CN, halogen, or an aromatic, aliphatic or araliphatic group with up to 50 C atoms;
- X is in each case independently —O—, —S—, —CO—, —COO—, —OCO—, —OCO—O, —CO—NH—, —NH—CO—, —OCH$_2$—, —CH$_2$=CH—, —C≡C, —SCH$_2$—, —CH$_2$S—, —CH=CH—COO—, —OOC—CH=CH— or a single bond; and
- Y is in each case independently —CO—, —COO—, —CO—NH—, —CO—CH=CH— or a single bond.

31. A liquid crystal display comprising a liquid crystal medium containing a chiral compound, mixture or polymer of formula I

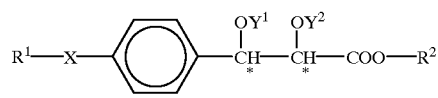

I wherein

C is a chiral carbon atom;

*

$Y^1$ is -Y-$R^3$ and $Y^2$ is -Y-$R^4$, or alternatively $Y^1$ and $Y^2$ together are —CO— or —C($XR^3$)($XR^4$)—;

$R^1$, $R^2$, $R^3$ and $R^4$ are independently of each other H, CN, halogen, or an aromatic, aliphatic or araliphatic group with up to 50 C atoms;

X is in each case independently —O—, —S—, —CO—, —COO—, —OCO—, —OCO—O, —CO—NH—, —NH—CO—, —OCH$_2$, —CH$_2$O—, —CH=CH—, —C≡C, —SCH$_2$—, —CH$_2$S—, —CH=CH—COO—, —OOC—CH=CH— or a single bond; and Y is in each case independently —CO—, —COO—, —CO—NH—, —CO—CH=CH— or a single bond.

32. An SSCT or PSCT display comprising a liquid crystal medium containing a chiral compound, mixture or polymer of formula I

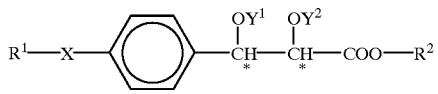

wherein

C is a chiral carbon atom;

*

$Y^1$ is -Y-$R^3$ and $Y^2$ is -Y-$R^4$, or alternatively $Y^1$ and $Y^2$ together are —CO— or —C($XR^3$)($XR^4$)—;

$R^1$, $R^2$, $R^3$ and $R^4$ are independently of each other H, CN, halogen, or an aromatic, aliphatic or araliphatic group with up to 50 C atoms;

X is in each case independently —O—, —S—, —CO—, —COO—, —OCO—, —OCO—O, —CO—NH—, —NH—CO—, —OCH$_2$—, —CH$_2$O—, —CH=CH—, —C≡C, —SCH$_2$—, —CH$_2$S—, —CH=CH—COO—, —OOC—CH=CH— or a single bond; and Y is in each case independently —CO—, —COO—, —CO—NH—, —CO—CH=CH— or a single bond.

33. A passive optical element selected from the group comprising polarizers, compensators, alignment layers, cholestric filters and holographic elements comprising a chiral compound, mixture or polymer of formula I

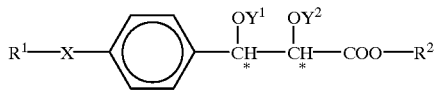

wherein

C is a chiral carbon atom;

*

$Y^1$ is -Y-$R^3$ and $Y^2$ is -Y-$R^4$, or alternatively $Y^1$ and $Y^2$ together are —CO— or —C($XR^3$)($XR^4$)—;

$R^1$, $R^2$, $R^3$ and $R^4$ are independently of each other H, CN, halogen, or an aromatic, aliphatic or araliphatic group with up to 50 C atoms;

X is in each case independently —O—, —S—, —CO—, —COO—, —OCO—, —OCO—O, —CO—NH—, —NH—CO—, —OCH$_2$—, —CH$_2$O—, —CH=CH—, —C≡C, —SCH$_2$—, —CH$_2$S—, —CH=CH—COO—, —OOC—CH=CH— or a single bond; and Y is in each case independently —CO—, —COO—, —CO—NH—, —CO—CH=CH— or a single bond.

34. In a liquid crystalline mixture comprising at least two liquid crystal compounds, the improvement wherein said mixture contains at least one compound according to claim 2.

35. A liquid crystalline mixture according to claim 34, further comprising at least one polymerizable mesogenic compound having at least one polymerizable functional group.

36. A chiral linear or crosslinked liquid crystalline polymeric material obtainable by polymerizing a mixture according to claim 35.

37. In a liquid crystal display containing a liquid crystalline mixture, the improvement wherein said liquid crystalline mixture is in accordance with claim 34.

38. A liquid crystal display according to claim 37, wherein said liquid crystalline mixture further comprising at least one polymerizable mesogenic compound having at least one polymerizable functional group.

39. In a method of preparing an active or passive optical element incorporating a liquid crystal material, the improvement wherein said material is a mixture according to claim 34.

40. A liquid crystal display according to claim 37, wherein said display is an SSCT or PSCT display.

41. In adhesive composition, cosmetic composition, diagnostic composition, liquid crystal pigment composition, or a synthetic resin composition having isotropic mechanical properties comprising at least one chiral compound, the improvement wherein the composition contains a chiral compound according to claim 2.

42. A liquid crystal display comprising a liquid crystal medium containing a chiral compound, mixture or polymer of claim 2.

43. An SSCT or PSCT display comprising a liquid crystal medium containing a chiral compound, mixture or polymer of claim 2.

44. A passive optical element selected from the group comprising polarizers, compensators, alignment layers, cholestric filters and holographic elements comprising a chiral compound, mixture or polymer of claim 2.

45. In a liquid crystalline mixture comprising at least two liquid crystal compounds, wherein said mixture contains at least one compound according to claim 7.

46. A liquid crystalline mixture according to claim 45, further comprising at least one polymerizable mesogenic compound having at least one polymerizable functional group.

47. A chiral linear or crosslinked liquid crystalline polymeric material obtainable by polymerizing a mixture according to claim 46.

48. In a liquid crystal display containing a liquid crystalline mixture, the improvement wherein said liquid cyrstalline mixture is in accordance with claim 45.

49. A liquid crystal display according to claim 48, wherein said liquid crystalline mixture further comprising at least one polymerizable mesogenic compound having at least one polymerizable functional group.

50. In a method of preparing an active or passive optical element incorporating a liquid crystal material, the improvement wherein said material is a mixture according to claim 45.

51. A liquid crystal display according to claim 48, wherein said display is an SSCT or PSCT display.

52. In adhesive composition, cosmetic composition, diagnostic composition, liquid crystal pigment composition, or a synthetic resin composition having isotropic mechanical properties comprising at least one chiral compound, the improvement wherein the composition contains a chiral compound according to claim 7.

53. A liquid crystal display comprising a liquid crystal medium containing a chiral compound, mixture or polymer of claim 7.

54. An SSCT or PSCT display comprising a liquid crystal medium containing a chiral compound, mixture or polymer of claim 7.

55. A passive optical element selected from the group comprising polarizers, compensators, alignment layers, cholestric filters and holographic elements comprising a chiral compound, mixture or polymer of claim 7.

56. A chiral compound to claim 2, wherein at least one of $R^1$ and $R^2$ is of formula I*

-(Sp-X)$_n$-MG-R        I*.

57. A chiral compound according to claim 5, wherein said compound is formula Ia, Ib, or Ic::

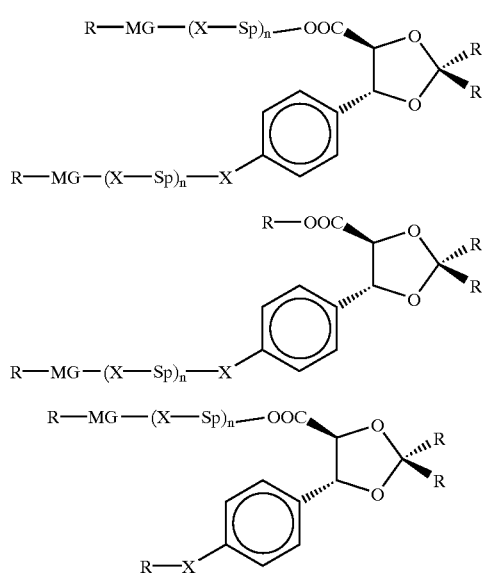

58. A chiral compound according to claim 3, wherein MG is at least one of:

| | |
|---|---|
| -Phe- | II-1 |
| -Cyc- | II-2 |
| -PheL- | II-3 |
| -Phe-Z-Phe- | II-4 |
| -Phe-Z-Cyc- | II-5 |
| -Cyc-Z-Cyc- | II-6 |
| -PheL-Z-Phe- | II-7 |
| -PheL-Z-Cyc- | II-8 |
| -PheL-Z-PheL- | II-9 |
| -Phe-Z-Phe-Z-Phe- | II-10 |
| -Phe-Z-Phe-Z-Cyc- | II-11 |
| -Phe-Z-Cyc-Z-Phe- | II-12 |
| -Cyc-Z-Phe-Z-Cyc- | II-13 |
| -Phe-Z-Cyc-Z-Cyc- | II-14 |
| -Cyc-Z-Cyc-Z-Cyc- | II-15 |
| -Phe-Z-Phe-Z-PheL- | II-16 |

-continued

| | |
|---|---|
| -Phe-Z-PheL-Z-Phe- | II-17 |
| -PheL-Z-Phe-Z-PheL- | II-18 |
| -PheL-Z-PheL-Z-Phe- | II-19 |
| -PheL-Z-PheL-Z-PheL- | II-20 |
| -Phe-Z-PheL-Z-Cyc- | II-21 |
| -Phe-Z-Cyc-Z-PheL- | II-22 |
| -Cyc-Z-Phe-Z-PheL- | II-23 |
| -PheL-Z-Cyc-Z-PheL- | II-24 |
| -PheL-Z-PheL-Z-Cyc- | II-25 |
| -PheL-Z-Cyc-Z-Cyc- | II-26 |
| -Cyc-Z-PheL-Z-Cyc- | II-27 | wherein

Z is —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH═CH—, —CH—CH—COO, —OCO—CH═CH—, —C═C—, or a single bond, Phe is 1,4-phenylene, PheL is a 1,4-phenylene group which is substituted by at least one group L, L is F, CL, CN, NO$_2$ or an optionally fluorinated alkyl, alkoxy, or alkanoyl group with 1 to 4 C atoms, and Cyc is 1,4-cyclohexylene.

59. A chiral compound according to claim 3, wherein MG is at least one of:

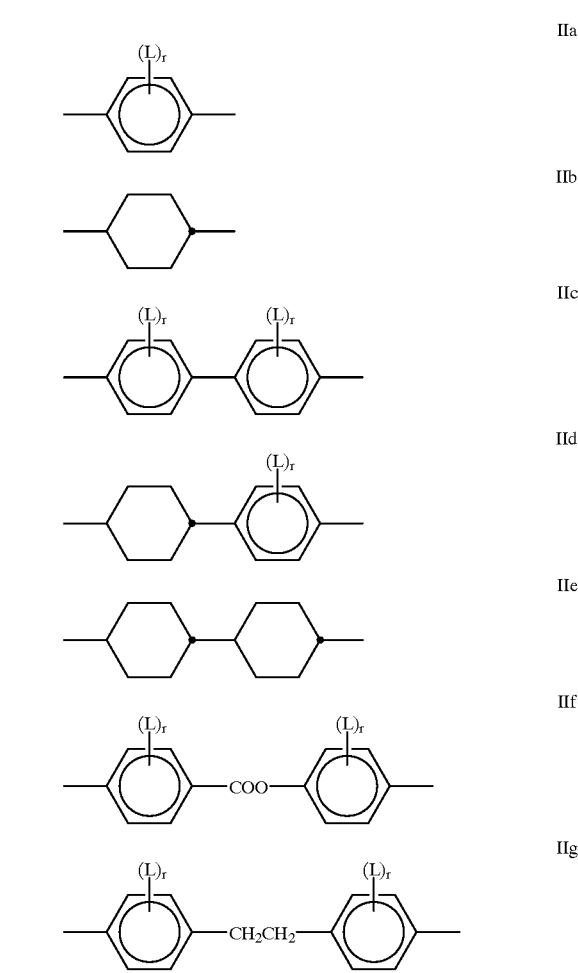

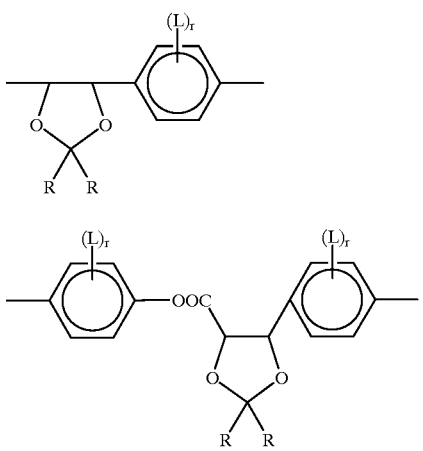

IIh

IIi wherein
L is F, CL, CN, $NO_2$ or an optionally fluorinated alkyl, alkoxy or alkanoyl group with 1 to 4 C atoms, and r is 0, 1 or 2.

60. A chiral compound according to claim 1, wherein at least one of each of $R^1$, $R^2$, $R^3$ and $R^4$ is of formula III

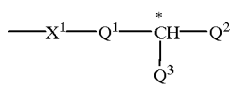

III having up to 25 carbon atoms,
wherein
$X^1$ is —O—, —S—, —CO—, —COO—, —OCO—, —OCOO— or a single bond,
$Q^1$ is alkylene having 1 to 10 C atoms, alkyleneoxy having 1 to 10 C atoms, or a single bond;
$Q^2$ is alkyl or alkoxy having in each case 1 to 10 C atoms, wherein the alkyl or alkoxy is unsubstituted, mono- or polysubstituted by halogen or CN, and wherein one or more non-adjacent $CH_2$ groups can be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another,
$Q^3$ is halogen, CN, alkyl having 1 to 4 C atoms, wherein $Q^3$ is different from $Q^2$.

61. In a liquid crystalline mixture comprising at least two liquid crystal compounds, the improvement wherein said mixture contains at least one chiral compound of formula I

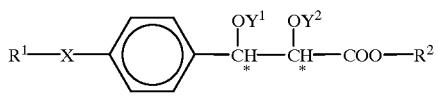

I wherein
C is a chiral carbon atom;
$Y^1$ is -Y-$R^3$ and $Y^2$ is -Y-$R^4$, or alternatively $Y^1$ and $Y^2$ together are —CO— or —C($XR^3$)($XR^4$)—;
$R^1$, $R^2$, $R^3$ AND $R^4$ are independently of each other H, CN, halogen, or an aromatic, aliphatic or araliphatic group with up to 50 C atoms;

X is in each case independently —O—, —S—, —CO—, —COO—, —OCO—, —OCO—O, —CO—NH—, —NH—CO—, —O$CH_2$—, —$CH_2$O—, —CH=CH—, —C≡C, —S$CH_2$—, —$CH_2$S—, —CH=CH—COO—, —OOC—CH=CH—or a single bond; and
Y is in each case independently —CO—, —COO—, —CO—NH—, —CO—CH=CH— or a single bond
wherein
a) if $Y^1$ and $R^1$-X are each H and $Y^2$ is phenyl, then $R^2$ is not H or $CH_3$; and
b) if $Y^1$ is Y—$R^3$ and $Y^2$ is Y—$R^4$, then Y—$R^3$ and Y—$R^4$ are not both H, or
c) when $Y^1$ and $Y^2$ together are —C($XR^3$)($XR^4$)—, then at least one of $R^1$, $R^2$, $R^3$ and $R^4$ is of formula I*

-(Sp-X)$_n$-MG-R    I* wherein
Sp is in each case independently a spacer group with 1 to 20 C atoms;
n is 0 or 1;
MG is a bicyclic or tricyclic mesogenic group;
R is in each case independently H, CN, halogen, a straight-chain or branched-chain alkyl having up to 25 C atoms which is unsubstituted, or mono- or polysubstituted by halogen or CN, or a straight-chain or branched-chain alkyl having up to 25 C atoms in which one or more nonadjacent $CH_2$ groups, in each case independently from one another, replaced by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another and which is unsubstituted, or mono- or polysubstituted by halogen or CN, or R can also be in each case independently P-(Sp-X)$_n$; and
P is a polymerizable group.

62. In an adhesive composition, cosmetic composition, diagnostic composition, liquid crystal pigment composition, or a synthetic resin composition having isotropic mechanical properties comprising at least one chiral compound, the improvement wherein the composition contains a chiral compound of formula I

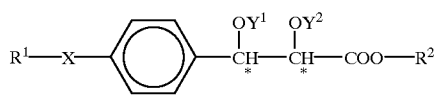

I wherein
C is a chiral carbon atom;
$Y^1$ is -Y-$R^3$ and $Y^2$ is -Y-$R^4$, or alternatively $Y^1$ and $Y^2$ together are —CO— or —C($XR^3$)($XR^4$)—;
$R^1$, $R^2$, $R^3$ and $R^4$ are independently of each other H, CN, halogen, or an aromatic, aliphatic or araliphatic group with up to 50 C atoms;
X is in each case independently —O—, —S—, —CO—, —COO—, —OCO—, —OCO—O, —CO—NH—, —NH—CO—, —O$CH_2$—, —$CH_2$O—, —CH=CH—, —C≡C, —S$CH_2$—, —$CH_2$S—, —CH=CH—COO—, —OOC—CH=CH— or a single bond; and Y is in each case independently —CO—, —COO—, —CO—NH—, —CO—CH=CH— or a single bond
wherein
a) if $Y^1$ and $R^1$-X are each H and $Y^2$ is phenyl, then $R^2$ is not H or $CH_3$; and
b) if $Y^1$ is Y-$R^3$ and $Y^2$ is Y-$R^4$, then Y-$R^3$ and Y-$R^4$ are not both H, or
c) when $Y^1$ and $Y^2$ together are —C($XR^3$)($XR^4$)—, then at least one of $R^1$, $R^2$, $R^3$ and $R^4$ is of formula I*

-(Sp-X)$_n$-MG-R     I* wherein
Sp is in each case independently a spacer group with 1 to 20 C atoms;
n is 0 or 1;
MG is a bicyclic or tricyclic mesogenic grouop;
R is in each case independently H, CN, halogen, a straight-chain or branched-chain alkyl having up to 25 C atoms which is unsubstituted, or mono- or polysubstituted by halogen or CN, or a straight-chain or branched-chain alkyl having up to 25 C atoms in which one or more nonadjacent $CH_2$ groups is, in each case independently from one another, replaced by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another and which is unsubstituted, or mono- or polysubstituted by halogen or CN, or R can also be in each case independently P-(Sp-X)$_n$; and
P is a polymerizable group.

63. A liquid crystal display comprising a liquid crystal medium containing a chiral compound, mixture or polymer of formula I

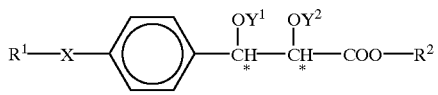

wherein
C is a chiral carbon atom;
$Y^1$ is -Y-$R^3$ and $Y^2$ is -Y-$R^4$, or alternatively $Y^1$ and $Y^2$ together are —CO— or —C($XR^3$)($XR^4$)—;
$R^1$, $R^2$, $R^3$ and $R^4$ are independently of each other H, CN, halogen, or an aromatic, aliphatic or araliphatic group with up to 50 C atoms;
X is in each case independently —O—, —S—, —CO—, —COO—, —OCO—, —OCO—O, —CO—NH—, —NH—CO—, —OCH$_2$—, —CH$_2$O—, —CH=CH—, —C≡C, —SCH$_2$—, —CH$_2$S—, —CH=CH—COO—, —OOC—CH=CH— or a single bond; and
Y is in each case independently —CO—, —COO—, —CO—NH—, —CO—CH=CH— or a single bond
wherein
a) if $Y^1$ and $R^1$ -X are each H and phenyl, then $R^2$ is not H or $CH_3$; and
b) if $Y^1$ is Y-$R^{-3}$ and $Y^2$ is Y-$R^4$, then Y-$R^3$ and Y-$R^4$ are not both H, or
c) when $Y^1$ and $Y^2$ together are —C($XR^3$)($XR^4$)—, then at least one of $R^1$, $R^2$, $R^3$ and $R^4$ is of formula I*

-(Sp-X)$_n$-MG-R     I* wherein
Sp is in each case independently a spacer group with 1 to 20 C atoms;
n is 0 or 1;
MG is a bicyclic or tricyclic mesogenic group;
R is in each case iindependently H, CN, halogen, a straight-chain or branched-chain alkyl having up to 25 C atoms which is unsubstituted, or mono- or polysubstituted by halogen or CN, or a straight-chain or branched-chain alkyl having up to 25 C atoms in which one or more nonadjacent $CH_2$ groups is, in each case independently from one another, replaced by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another and which is unsubstituted, or mono- or polysubstituted by halogen or CN, or R can also be in each case independently P-(Sp-X)$_n$; and
P is a polymerizable group.

64. An SSCT or PSCT display comprising a liquid crystal medium containing a chiral compound, mixture of polymer of formula I

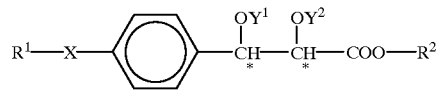

wherein
C is a chiral carbon atom;
$Y^1$ is -Y-$R^3$ and $Y^2$ is -Y-$R^4$, or alternatively $Y^1$ and $Y^2$ together are —CO— or —C($XR^3$)($XR^4$)—;
$R^1$, $R^2$, $R^3$ and $R^4$ are independently of each other H, CN, halogen, or an aromatic, aliphatic or araliphatic group with up to 50 C atoms;
X is in each case independently —O—, —S—, —CO—, —COO—, —OCO—, —OCO—O, —CO—NH—, —NH—CO—, —OCH$_2$—, —CH$_2$O—, —CH=CH—, —C≡C, —SCH$_2$—, —CH$_2$S—, —CH=CH—COO—, —OOC—CH=CH— or a single bond; and
Y is in each case independently —CO—, —COO—, —CO—NH—, —CO—CH=CH— or a single bond
wherein
a) if $Y^1$ and $R^1$ -X are each H and $Y^2$ is phenyl, then $R^2$ is not H or $CH_3$; and
b) if $Y^1$ is Y-$R^3$ and $Y^2$ is Y-$R^4$, then Y-$R^3$ and Y-$R^4$ are not both H, or
c) when $Y^1$ and $Y^2$ together are —C($XR^3$)($XR^4$)—, then at least one of $R^1$, $R^2$, $R^3$ and $R^4$ is of formula I*

-(Sp-X)$_n$-MG-R     I* wherein
Sp is in each case independently a spacer group with 1 to 20 C atoms;
n is 0 or 1;
MG is a bicyclic or tricyclic mesogenic group;

R is in each case independently H, CN, halogen, a straight-chain or branched-chain alkyl having up to 25 C atoms which is unsubstituted, or mono- or polysubstituted by halogen or CN, or a straight-chain or branched-chain alkyl having up to 25 C atoms in which one or more nonadjacent $CH_2$ groups is, in each case independently from one another, replaced by —O—, —S—, —NH—, —N($CH_3$)—, —CO—, —COO—, —OCO—, —OCO—O—, —S—CO—, —CO—S— or C≡C— in such a manner that oxygen atoms are not linked directly to one another and which is unsubstituted, or mono- or polysubstituted by halogen or CN, or R can also be in each case independently P-(Sp-X)$_n$; and P is a polymerizable group.

65. A passive optical element selected from the group comprising polarizers, compensators, alignment layers, cholestric filters and holographic elements comprising a chiral compound, mixture or polymer of formula I

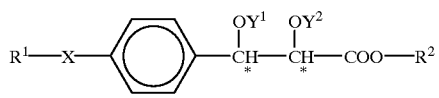  I wherein

C is a chiral carbon atom;

$Y^1$ is -Y-$R^3$ and $Y^2$ is -Y-$R^4$, or alternatively $Y^1$ and $Y^2$ together are —CO— or —C($XR^3$)($XR^4$)—;

$R^1$, $R^2$, $R^3$ and $R^4$ are independently of each other H, CN, halogen, or an aromatic, aliphatic or araliphatic group with up to 50 C atoms;

X is in each case independently —O—, —S—, —CO—, —COO—, —OCO—, —OCO—O, —CO—NH—, —NH—CO—, —O$CH_2$—, —$CH_2$O—, —CH=CH—, C≡C, —S$CH_2$, —$CH_2$S—, —CH=CH—COO—, —OOC—CH=CH— or a single bond; and Y is in each case independently —CO—, —COO—, —CO—NH—, —CO—CH=CH— or a single bond wherein a) if $Y^1$ and $R^1$ -X are each H and $Y^2$ is phenyl, then $R^2$ is not H or $CH_3$; and b) if $Y^1$ is Y-$R^3$ and $Y^2$ is Y-$R^4$, then Y-$R^3$ and Y-$R^4$ are not both H, or c) when $Y^1$ and $Y^2$ together are —C($XR^3$)($XR^4$)—, then at least one of $R^1$, $R^2$, $R^3$ and $R^4$ is of formula I*

$-(Sp-X)_n-MG-R$  I* wherein

Sp is in each case independently a spacer group with 1 to 20 C atoms;

n is 0 or 1;

MG is a bicyclic or tricyclic mesogenic group;

R is in each case independently H, CN, halogen, a straight-chain or branched-chain alkyl having up to 25 C atoms which is unsubstituted, or mono- or polysubstituted by halogen or CN, or a straight-chain or branched-chain alkyl having up to 25 C atoms in which one or more nonadjacent $CH_2$ groups is, in each case independently from one another, replaced by —O—, —S—, —NH—, —N($CH_3$)—, —CO—, —COO—, —OCO—, —OCO—O—, —S—CO—, —CO—S—, or —C≡C— in such manner that oxygen atoms are not linked directly to one another and which is unsubstituted, or mono- or polysubstituted by halogen or CN, or R can also be in each case independently P-(Sp-X)$_n$; and P is a polymerizable group.

* * * * *

UNITED STATES PATENT AND TRADEMARK OFFICE
CERTIFICATE OF CORRECTION

PATENT NO. : 6,495,217 B2
APPLICATION NO. : 09/411380
DATED : December 17, 2002
INVENTOR(S) : Louise Farrand It is certified that error appears in the above-identified patent and that said Letters Patent is hereby corrected as shown below:

Column 27, line 31, reads "-COO-, -OCO-O," should read
-- -COO-, -OCO-, -OCO-O-, --
Column 27, line 33, reads "-C≡C," should read -- -C≡C-, --
Column 27, line 57, reads "staight-chain" should read -- straight-chain --
Column 27, line 67, reads ".; and" should read -- ; and --
Column 28, line 14, reads "$Y^1$ and" should read -- $Y^1$ and $Y^2$ --
Column 28, line 20, reads "-OCO-O," should read -- -OCO-O-, --
Column 28, line 22, reads "-C≡C," should read -- -C≡C-, --
Column 28, line 29, reads "-(Sp-X)$_n$-Mg-R" should read -- -(Sp-X)$_n$-MG-R --
Column 28, line 53, reads "formula II." should read -- formula II --
Column 28, line 60-61, reads "-OCO-CH=CH," should read -- -OCO-CH=CH-, --
Column 28, line 61, reads "single bond:" should read -- single bond; --
Column 29, line 3, reads "piperidine-1,4-diyl naphthalene-2,6-diyl," should read
-- piperidine-1,4-diyl, naphthalene-2,6-diyl, --
Column 29, line 8, reads "gruops" should read -- groups --
Column 29, line 59, reads " $\overset{C}{*}$ is a chiral atom;" should read -- $\overset{C}{*}$ is a chiral carbon atom; --
Column 29, line 67, reads "-OCO-O-O," should read -- -OCO-O-, --
Column 30, line 2, reads "-C≡C," should read -- -C≡C-, --
Column 30, line 8, reads "is wherein" should read -- is R wherein --
Column 30, line 44, reads "further comprising" should read -- further comprises --
Column 30, line 47, reads "accrding to" should read -- according to --

Column 30, line 48-53, delete lines and insert -- 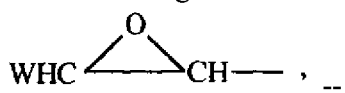 , --
Column 30, line 64, reads "-CH(halogen)-, -CH=CH-or" should read -- -CO-O-, -CH(halogen)-, -CH(CN)-, -CH=CH- or --
Column 31, line 22, reads "cholestric" should read -- cholesteric --
Column 31, line 46, reads "cyrstalline" should read -- crystalline --
Column 31, line 67, reads "-COC-O-," should read -- -OCO-O-, --
Column 32, line 2, reads "-C≡C," should read -- -C≡C-, --
Column 32, line 18, reads "further comprising" should read -- further comprises --
Column 32, line 27, reads "In adhesive" should read -- In an adhesive --
Column 32, line 44, reads "is –Y-$R^3$" should read -- $Y^1$ is -Y-$R^3$ --
Column 32, line 44, reads "$Y^2$ is –Y-$Y^4$" should read -- $Y^2$ is -Y-$R^4$ --
Column 32, line 50, reads "-OCO-O," should read -- -OCO-O-, --
Column 32, line 51, reads "-CH$_2$=CH-, -C≡C," should read -- -CH=CH-, -C≡C-, --

UNITED STATES PATENT AND TRADEMARK OFFICE
CERTIFICATE OF CORRECTION

PATENT NO. : 6,495,217 B2
APPLICATION NO. : 09/411380
DATED : December 17, 2002
INVENTOR(S) : Louise Farrand It is certified that error appears in the above-identified patent and that said Letters Patent is hereby corrected as shown below:

Column 33, line 10, reads "-OCO-O," should read -- -OCO-O-, --
Column 33, line 11, reads "-OCH$_2$," should read -- -OCH$_2$-, --
Column 33, line 12, reads "-C≡C," should read -- -C≡C-, --
Column 33, line 36, reads "-OCO-O," should read -- -OCO-O-, --
Column 33, line 38, reads "-C≡C," should read -- -C≡C-, --
Column 33, line 45, reads "cholestric" should read -- cholesteric --
Column 34, line 20, reads "further comprising" should read -- further comprises --
Column 34, line 29, reads "In adhesive" should read -- In an adhesive --
Column 34, line 43, reads "cholestric" should read -- cholesteric --
Column 34, line 57, reads "cyrstalline" should read -- crystalline --
Column 34, line 59, reads "further comprising" should read -- further comprises --
Column 35, line 1, reads "In adhesive" should read -- In an adhesive --
Column 35, line 15, reads "cholestric" should read -- cholesteric --
Column 35, line 17, reads "compound to" should read -- compound according to --
Column 35, line 24, reads "formula" should read -- is of formula --
Column 35, line 24, reads "Ic::" should read -- Ic: --
Column 36, line 20, reads "-C=C-," should read -- -C≡C-, --
Column 36, line 24, reads "F, CL," should read -- F, Cl, --
Column 37, lines 1-20, delete
Column 37, line 22, reads "F, CL," should read -- F, Cl, --
Column 37, line 37, reads "-OCOO-" should read -- -O-COO- --
Column 37, line 46, reads "-S-CO-or" should read -- -S-CO- or --
Column 37, line 48, reads "atoms, wherein" should read -- atoms, or alkoxy having 1 to 4 C atoms, wherein --
Column 37, line 62, reads "C is" should read -- $\overset{C}{*}$ is --
Column 37, line 65, reads "R$^3$ AND R$^4$" should read -- R$^3$ and R$^4$ --
Column 38, line 5, reads "-OOC-CH=CH-or" should read -- -OOC-CH=CH- or --
Column 38, line 56, reads "C is" should read -- $\overset{C}{*}$ is --
Column 39, line 46, reads "C is" should read -- $\overset{C}{*}$ is --
Column 39, line 53, reads "-OCO-O," should read -- -OCO-O-, --
Column 39, line 55, reads "-C≡C," should read -- -C≡C-, --
Column 39, line 62, reads "and phenyl" should read -- and Y$^2$ is phenyl --
Column 39, line 64, reads "Y-R-$^3$" should read -- Y-R$^3$ --
Column 40, line 10, reads "iindependently" should read -- independently --
Column 40, line 26, reads "mixture of polymer" should read -- mixture or polymer

UNITED STATES PATENT AND TRADEMARK OFFICE
CERTIFICATE OF CORRECTION

PATENT NO. : 6,495,217 B2
APPLICATION NO. : 09/411380
DATED : December 17, 2002
INVENTOR(S) : Louise Farrand It is certified that error appears in the above-identified patent and that said Letters Patent is hereby corrected as shown below:

Column 40, line 37, reads "C is" should read -- $\overset{C}{*}$ is --
Column 40, line 44, reads "-OCO-O," should read -- -OCO-O-, --
Column 40, line 46, reads "-C≡C," should read -- -C≡C-, --
Column 41, line 9, reads "-OCO-O," should read -- -OCO-O-, --
Column 41, line 10, reads "C≡C-" should read -- -C≡C- --
Column 41, line 17, reads "cholestric" should read -- cholesteric --
Column 41, line 28, reads "C is" should read -- $\overset{C}{*}$ is --
Column 41, line 35, reads "-OCO-O," should read -- -OCO-O-, --
Column 41, line 37, reads "C≡C, -SCH$_2$," should read -- -C≡C-, -SCH$_2$-, --

Signed and Sealed this

Fifteenth Day of December, 2009

David J. Kappos
*Director of the United States Patent and Trademark Office*